(12) United States Patent
Shibata et al.

(10) Patent No.: US 6,872,803 B1
(45) Date of Patent: Mar. 29, 2005

(54) PEPTIDES

(75) Inventors: Kenji Shibata, Kawagawa (JP); Toshiyuki Suzawa, Kanagawa (JP); Motoo Yamasaki, Tokyo (JP); Koji Yamada, Kanagawa (JP); Tatsuhiro Ogawa, Kanagawa (JP); Takeo Tanaka, Tokyo (JP); Shiro Soga, Tokyo (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/349,707

(22) Filed: Jul. 8, 1999

Related U.S. Application Data

(63) Continuation of application No. 08/433,404, filed on May 18, 1995, now abandoned.

(30) Foreign Application Priority Data

Sep. 21, 1993 (JP) .............................................. 5-235152

(51) Int. Cl.⁷ .............................................. A61K 38/10
(52) U.S. Cl. ...................... 530/317; 530/307; 530/326; 530/327; 530/328; 530/329; 514/9; 514/10; 514/11; 514/12; 514/13; 514/14; 514/15; 514/16; 930/60
(58) Field of Search ................... 514/9–16; 530/317, 530/307, 326–329; 930/60

(56) References Cited

U.S. PATENT DOCUMENTS 4,757,048 A 7/1988 Lewicki et al. ............... 514/11

FOREIGN PATENT DOCUMENTS

| EP | 0 323 740 | 7/1989 |
|---|---|---|
| EP | 0 415 219 | 3/1991 |
| EP | 0 461 869 | 12/1991 |
| EP | 0 536 741 | 4/1993 |
| EP | 0 564 739 | 10/1993 |
| EP | 0 603 399 | 6/1994 |
| JP | 6157588 | 6/1994 |
| WO | 90 02751 A | 3/1990 |
| WO | 92 17201 A | 10/1992 |
| WO | 92/17492 | 10/1992 |
| WO | 93 132218 | 7/1993 |
| WO | 94 05310 A | 3/1994 |
| WO | 95 00546 A | 1/1995 |
| WO | 95/00546 | 1/1995 |

OTHER PUBLICATIONS

Kirby et al., "Defining Structural Requirements for Neuropeptide Y Receptors Using Truncated and Conformationally Restricted Analogues", J. Med. Chem. 36:385–393 (1993).

Wyss et al., "Anantin—A Peptide Antagonist of the Atrial Natriuretic Factor (ANF)", The Journal of Antibiotics 44(2):172–180 (1991).

*Primary Examiner*—Bennett Celsa
(74) *Attorney, Agent, or Firm*—Nixon & Vanderhye P.C.

(57) ABSTRACT

The present invention provides peptides represented by the following formula (A):

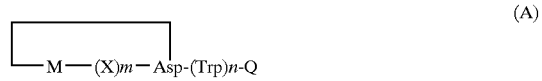

(A)

wherein Q represents a physiologically active peptide moiety; X each represents the same or different α-amino acid residue; M represents Gly or Cys; m represents an integer of from 5 to 8; and n represents an integer of from 0 to 3, or their pharmaceutically acceptable salts thereof.

The peptides of the present invention have higher stability and/or higher activity than physiologically active linear peptides to which no cyclic peptide is bonded.

10 Claims, 6 Drawing Sheets

US 6,872,803 B1

PEPTIDES

This is a continuation of application Ser. No. 08/433,404, filed May 18, 1995, abandoned, which is a U.S. national phase of PCT/JP94/01554, filed Sep. 21, 1994.

FIELD OF THE INVENTION

The present invention relates to novel peptides in which acyclic peptide having a particular structure is bonded to a physiologically active peptide optionally via a spacer. The peptides of the present invention have higher stability and/or higher activity than physiologically active linear peptides to which no cyclic peptide is bonded.

Examples of physiologically active peptides include peptides having cell adhesion-inhibiting activity, protein-farnesyltransferase-inhibiting peptides, peptides binding to atrial natriuretic peptide receptors, bradykinin-antagonistic peptides, etc. Peptides having cell adhesion-inhibiting activity generally inhibit the binding of fibrin and other proteins to platelets and blood cells, while participating in controlling adhesion of cells, and are therefore useful as medicines for treating platelet agglutination, osteoporosis, inflammation, etc. Protein-farnesyltransferase-inhibiting peptides generally inhibit the farnesylation of proteins, while participating in controlling the differentiation and the growth of cells, and are therefore useful as medicines for treating cancer and arteriosclerosis. Peptides binding to atrial natriuretic peptide receptors generally bind to natriuretic peptide receptors, while participating in controlling blood pressure and the amount of body fluid, and are therefore useful as medicines for treating cardiac insufficiency, renal insufficiency, hypertension, edema, etc. Bradykinin-antagonistic peptides generally have bradykinin-antagonistic activity and are therefore useful as medicines for treating hypertension, inflammation, pain, asthma, sepicemia, etc.

BACKGROUND ART

It is known that many physiologically active linear peptides do not have uniform conformation in solutions and have poor stability to protease. In order to solve these problems, cyclic peptide derivatives which are intended to have fixed conformation have been proposed.

For instance, cyclic peptides of somatostatin have been reported to have an elevated activity and improved stability as compared with the corresponding linear peptides [Nature, 292, 55 (1981)].

Cyclic peptides derived from peptides portions of gallanin have stabilized conformation, but it has been reported that their activity is noticeably lowered [Int. J. Peptide Protein Res., 38, 267 (1991)].

It is known that a peptide having a sequence of Arg-Gly-Asp (RGD) participates in the binding of integrin. Disorders caused by adhesion of cells' via integrin include platelet thrombosis, vascular re-obstruction, osteoporosis, inflammation, etc. Peptides which inhibit the binding of integrin through RGD sequence are useful as medicines for treating the disorders [Endocrinology, 132 (3), 1411 (1993); J. Cell Biology, 111, 1713 (1990); J. Bone and Mineral Research, 8, 239 (1993); Science, 233, 467 (1986); Tissue Culture, 15 (14), 486 (1989); Br. J. Cancer, 60, 722 (1989); Jpn. J Cancer Res., 81, 668 (1990); Cell, 65, 359 (1991); Science, 260, 906 (1993); Experimental Medicine, 10 (11), 76 (1992)].

Regarding RGD-related peptides, sequences of portions of human fibronectin mentioned below are known [Nature 350, 66 (1991)]:

H-Val-Thr-Gly-Arg-Gly-Asp-Ser-Pro-OH (SEQ ID NO:1)

H-Val-Tyr-Ala-Val-Thr-Gly-Arg-Gly-Asp-Ser-Pro-Ala-OH (SEQ ID NO:2)

Regarding RGD-related peptides, a cyclic peptide, cyclic (-Arg-Gly-Asp-D-Phe-Val-), has been reported to have an elevated activity of from 20 to 100 times the activity of Gly-Arg-Gly-Asp-Ser [FEBS Lett. 291, 50 (1991)].

Naturally occurring snake venom peptides are known having a Cys-Cys cyclic structure, trigramin (72 residues) [Biochemistry, 28, 661 (1989)], albolarin (73 residues), flavoridin (65 residues) [Biochemistry, 30, 5225 (1991)], etc. These have an activity of about, 1000 times higher than the activity of Gly-Arg-Gly-Asp-Ser (SEQ ID NO:3). In addition, the following cyclic peptides having a structure derived from these are known (JP-A-5-70364):

```
    ┌─────────────────────────────────────────┐
X-Cys-R-R-R-Arg-Gly-Asp-R-R-R-R-Cys-Y (SEQ ID
                                       NO:4)
``` wherein X represents H, or at least one amino acid residue; Y represents OH, or at least one amino acid residue; R represents the same or a different amino acid residue.

In addition, there are various reports referring to cyclic Arg-Gly-Asp-related peptides [Biochem. Biophys. Res. Commun., 177, 74 (1991); Angew. Chem., 104, 341 (1992); Tetrahedron Lett., 33, 1479 (1992); J. Chem. Soc. Perkin Trans., 2, 601 (1991); Cancer Lett., 65, 259 (1992); J. Med. Chem., 35, 3962 (1992); U.S. Pat. No. 4,683,291; WO89-05150; EP-A-0319506; EP-A-0341915; JP-A-4-506803].

It is known that the farnesylating modification of proteins is catalyzed by farnesyltransferase (FTase). Ras proteins that are activated by the modification participate in controlling the differentiation and the growth of cells. It is believed that if the control is disrupted by a mutation, cells undergo transformation and cancer results. Therefore, substances capable of inhibiting the farnesylation of proteins are useful as carcinostatics.

FTase is an enzyme which specifically recognizes an amino acid sequence comprising the C-terminal four residues of a protein, C-a1-a2-X (where C is a cysteine residue; a1 and a2 each are an aliphatic amino acid residue; and X is an amino acid residue), while acting to transfer the farnesyl group of farnesylpyrophosphoric acid into a cysteine residue.

Many peptides having the C-terminal sequence C-a1-a2-X which is recognized by FTase have been reported to be FTase inhibitors. [Cell, 62, 81 (1990); J. Biol. Chem., 265, 14701 (1990); ibid., 266, 15575 (1991); Proc. Natl. Acad. Sci. USA, 88, 732 (1991); ibid., 89, 8313 (1992); JP-A-6-157589 and JP-A-6-157590; Cell, 57, 1167 (1989); Protein, Nucleic Acid and Enzyme, 38, 1695 (1993)].

For example, peptides having the following sequences are known:

H-Cys-Met-Gly-Leu-Pro-Cys-Val-Val-Met-OH (SEQ ID NO:5)

[Cell 57, 1167 (1989); Protein Nucleic Acid and Enzyme, 38, 1695 (1993)]; and

H-Ser-Ser-Gly-Cys-Val-Leu-Ser-OH (SEQ ID NO:6)

[J. Biol. Chem., 265, 14701 (1990)].

In addition, analogues to these peptides have also been reported [J. Biol. Chem., 268, 18145 (1993); ibid., 268, 20695 (1993); ibid., 269, 12410 (1994); Science, 260, 1934 (1993); Bio. Med. Chem. Lett., 4, 887 (1994)].

Cyclic derivatives of FTase-inhibiting peptides have been reported to have an increased activity of from 10 to 50 times the activity of the original peptides [Science, 260, 1937 (1993)].

It is known that a natriuretic peptide derived from human atria (hereinafter referred to as ANP) expresses its physiological activity via two receptors GC-A and GC-B [Nature, 338, 78 (1989); Cell, 58, 1155 (1989); Nature, 341, 68 (1989)], and it is also known that ANP has diuretic activity and blood pressure-depressing activity as the main activities [Life Sci., 28, 89 (1981); Biochem. Biophys. Res. Commun., 118, 131 (1984); J. Clin. Invest., 84, 145 (1989)]. Therefore, ANP-agonists are useful as blood pressure-depressing diuretics.

In addition to the above-mentioned receptors, C-receptors which have no intracellular signal transmission domain are known. Such C-receptors do not exhibit their physiological activity even when ANP binds thereto, and it is considered that these act as clearance receptors for ANP [Science,. 238, 675 (1987); Cellular Signalling, 6, 125 (1994)]. Accordingly, it is believed that substances binding to C-receptors can increase the ANP concentration in blood by inhibiting the clearance for ANP and therefore exhibit the same effect as ANP agonists.

Many C-receptor-binding peptides have been reported, including peptide portions of ANP and derivatives thereof ["Peptide Regulation of Cardiovascular Function", pp. 65–77, Ed., Imura, Matuo and Masaki, Academic Press (1991); Eur. J. Pharmacol., 147, 49 (1988); J. Med. Chem., 32, 869 (1989); J. Biol. Chem., 2, 10989 (1.988); JP-A-3-50348; Int. J. Peptide Protein Res., 43, 332 (1994); WO94/14839; WO94/14840.

For example, in "Peptide Regulation of Cardiovascular Function", pp. 65–77, Ed., Imura, Matuo and Masaki, Academic Press (1991), a peptide having the following sequence corresponding to amino acids 8–15 of human ANP is disclosed:

H-Phe-Gly-Gly-Arg-Ile-Asp-Arg-Ile-NH$_2$ (SEQ ID NO:7), and a derivative of a peptide having a sequence corresponding to amino acids 7–18 of human ANP, wherein the 7th and 18th amino acids are substituted by alanines:

H-Ala-Phe-Gly-Gly-Arg-Ile-Asp-Arg-Ile-Gly-Ala-Ala-NH$_2$ (SEQ ID NO:8).

Cyclic derivatives of the peptides portions of ANP have been reported to have an increased receptor-binding activity of about two times the activity of the peptides portions of ANP [J. Med. Chem., 32, 67 (1989)].

Bradykinin (hereinafter referred to as BK) is an endogenous peptide having various physiological activities of, for example, vasoconstriction, bronchoconstriction, inflammatory reaction, algesiogenic transmission, etc., and this is considered to be one substance participating in the conditions of various disorders such as hypertension, inflammation, pain, asthma, septicemia, etc. Therefore, substances that are antagonistic to BK and inhibit the activities of BK are expected to be useful for treating and preventing these disorders.

There have been many reports that make reference to BK-antagonistic peptides ["Small peptides, Chemistry, Biology and Clinical Studies", pp. 83–102, Ed., A. S. Dutta, Elsevier (1993); "Peptides, Chemistry, Structure and Biology (Proceedings of the 13th American Peptide Symposium)", pp. 349–352, 353–355 and 449–451, Ed., Hodges and Smith, ESCOM (1994); Bio. Med. Chem. Lett., 4, 781 (1994)). For example, a BK-antagonistic peptide having the following sequence is known:

H-D-Arg-Arg-Pro-Hyp-Gly-Phe-Cys-D-Phe-Leu-Arg-OH (SEQ ID NO:72)

wherein Hyp represents a hydroxyproline ["Peptides, Chemistry, Structure and Biology (Proceedings of the 13th American Peptide Symposium)", pp. 349–352, 353–355 and 449–451, Ed., Hodges and Smith, ESCOM (1994)].

Cyclic BK-antagonistic peptides have been reported ["Peptides, Chemistry, Structure and Biology (Proceedings of the 13th American Peptide; Symposium)", pp. 381–383, 547–549, 550–552 and 687–689, Ed., Hodges and Smith, ESCOM (1994)].

However, there is no report referring to novel peptides provided by the present invention.

DESCRIPTION OF THE INVENTION

The present invention provides peptides of the following formula (A):

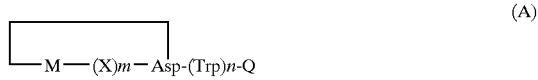

(A)

wherein Q represents a physiologically active peptide moiety; X represents the same or different α-amino acid residue; M represents Gly or Cys; m represents an integer of from 5 to 8; and n represents an integer of from 0 to 3, or pharmaceutically acceptable salts thereof.

The physiologically active peptide moiety represented by Q includes, for example, peptides having cell adhesion-inhibiting activity of the following formula (I):

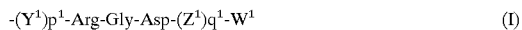

(I)

(wherein $Y^1$ and $Z^1$ each represent an α-amino acid residue; $W^1$ represents a hydroxy, lower alkoxy or amino group; $p^1$ represents an integer of from 0 to 5; $q^1$ represents an integer of from 0 to 10; and the α-amino acid residues to be represented by two or more $Y^1$'s when $p^1$ is 2 or more or by two or more $Z^1$'s when $q^1$ is 2 or more may be the same or different), protein-farnesyltransferase-inhibiting peptide residues of the following formula (II):

(II)

(wherein $A^2$, $B^2$ and $C^2$ each represent an α-amino acid residue; $p^2$ represents an integer of from 0 to 8; $Y^2$ and $W^2$ have the same meanings as the above-mentioned $Y^1$ and $W^1$, respectively; and the α-amino acid residues to be represented by two or more $Y^2$'s when $p^2$ is 2 or more may be the same or different), atrial natriuretic peptide receptor-binding peptide residues of the following formula (III):

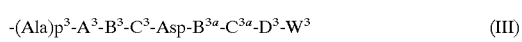

(III)

(wherein $p^3$ represents an integer of from 0 to 1; $W^3$ has the same meaning as the above-mentioned $W^1$; $A^3$ represents Phe, Gly, Phe-Gly, Gly-Gly, Phe-Gly-Gly or a single bond; $B^3$ and $B^{3a}$ may be the same or different and each represents Arg or D-Arg; $C^3$ and $C^{3a}$ may be the same or different and each represents Ile or (N-methyl)Ile; $D^3$ represents Gly, Ala, Gly-Ala, Ala-Ala, Gly-Ala-Ala or a single bond), and bradykinin-antagonistic peptide residues of the following formula (IV):

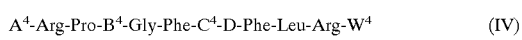

(IV)

(wherein, $A^4$ represents Arg, D-Arg or a single bond; $B^4$ represents a hydroxyproline or Pro; $C^4$ represents Ser or Cys; $W^4$ has the same meaning as the above-mentioned $W^1$).

The peptide compound represented by the above-mentioned formula (A) is hereinafter referred to as compound (A).

In the definitions referred to in the above-mentioned formulae (A), (I), (II), (III) and (IV), the alkyl moiety in the lower alkoxy group may be a linear or branched alkyl group having from 1 to 6 carbon atoms, including, for example, methyl, ethyl, propyl, isopropyl, butyl, isobutyl, sec-butyl, tert-butyl, pentyl, neopentyl, hexyl, isohexyl, etc.

As the α-amino acid residues mentioned are residues of natural amino acids and also residues of non-natural amino acids to be obtained by synthetic methods, including D- or L-alanine, asparagine, aspartic acid, arginine, cysteine, glutamine, glutamic acid, histidine, isoleucine, leucine, lysine, methionine, phenylalanine, proline, serine, threonine, tryptophan, tyrosine, valine and glycine, etc.

In the definitions referred to in the above-described formula (A), -(X)m includes, for example, -$X^1$-Trp-$X^2$-Gly-Thr-Ala-$X^3$- (SEQ ID NO:9) (wherein $X^1$ represents Asn or Asp; $X^2$ represents His or Lys; $X^3$ represents Pro or Ala), -Ser-Ala-Ala-Val-Tyr-Phe- (SEQ ID NO:10), -Phe-Ile-Gly-Trp-Gly-Asn- (SEQ ID NO:11), -Tyr-Pro-Trp-Trp-Asn-Tyr-Arg- (SEQ ID NO:12), -Leu-Gly-Val-Gly-Ser-$X^4$-Asn- (SEQ ID NO:13) (wherein $X^4$ represents Cys, Ala or Ser), etc.

In the definitions referred to in formula (I), -($Y^1$)$p^1$- includes, for example, -Gly-, -Pro-, -Cys-, -Arg-, -Lys-, -Arg-Ala-, -Phe-Pro-, -Pro-Lys-, -Gly-Arg-, -Ile-Pro-, -Met-Thr-, -Leu-Phe-, -Gly-Ser-Arg-, -Val-Thr-Gly-, -Ile-Cys-Lys-Arg-Ala- (SEQ ID NO:13), -Ile-Ser-Lys-Arg-Ala- (SEQ ID NO:14), -Ile-Ala-Lys-Arg-Ala- (SEQ ID NO:15), -Tyr-Ile-Gly-Ser-Arg- (SEQ ID NO:17), -Tyr-Ala-Val-Thr-Gly- (SEQ ID NO:18), -Val-Tyr-Ala-Val-Thr-Gly- (SEQ ID NO:19), -Lys-Gly-Thr-Ile-Cys-Arg-Arg-Ala- (SEQ ID NO:20) etc.; -($Z^1$)$q^1$- includes, for example, -Asp-, -Leu-, -Ile-, -Phe-, -Trp-, -Asp-Asp-, -Thr-Pro-, -Phe-Val-, -Phe-Leu-, -Ser-Lys-, -Phe-Gly-, -Ser-Pro-, -Cys-Leu-, -Leu-Pro-, -Leu-Arg-, -Leu-Gly-, -Gly-Trp-, -Gly-Phe-, -Phe-Val-Ala-, Phe-Val-Gly-, -Phe-Pro-Gly-, -Phe-Leu-Ala-, -Phe-Leu-Gly-, -Ser-Pro-Ala-, -Arg-Pro-Gly-, -Ser-Trp-Gly-, -Leu-His-Leu-, -Phe-Trp-Gln-, -Leu-Trp-Thr-, -Gly-Trp-Leu-, -Ser-Pro-Cys-Ala- (SEQ ID NO:21), -Ser-Pro-Ser-Ala- (SEQ ID NO:22), -Gly-Phe-Gly-Ser- (SEQ ID NO:23), -Asp-Leu-Asp-Asp-Tyr- (SEQ ID NO:24), -Asp-Asp-Met-Asp-Asp-Tyr- (SEQ ID NO:25), -Asp-Asp-Gly-Asp-Asp-Tyr- (SEQ ID NO:26), -Asp-Asp-Ser-Asp-Asp-Tyr- (SEQ ID NO:27), -Ser-Pro-Ala-Ser-Ser-Lys- (SEQ ID NO:28), -Asp-Leu-Asp-Asp-Tyr-Cys-Asn- (SEQ ID NO:29), -Asp-Leu-Asp-Asp-Tyr-Ser-Asn- (SEQ ID NO:30) etc.

In the definitions referred to in formula (II), $A^2$ and $B^2$ each are preferably an aliphatic amino acid residue or an aromatic amino acid residue, including amino acid residues such as Val, Ile, Leu, Phe, etc. $C^2$ includes amino acid residues such as Met, Ser, Leu, Gln, Asn, etc. -($Y^2$)$p^2$- includes, for example, -Ser-Ser-Gly-, -Ser-Met-Gly-Leu-Pro- (SEQ ID NO:31), -Gly-Ser-Met-Ser-Cys-Lys- (SEQ ID NO:32), -Gly-Ala-Met-Ser-Cys-Lys- (SEQ ID NO:33), -Cys-Val-Lys-Ile-Lys-Lys- (SEQ ID NO:34), -Lys-Lys-Ser-Lys-Thr-Lys- (SEQ ID NO:35) -Lys-Lys-Ser-Arg-Thr-Arg-Thr-Arg- (SEQ ID NO:36), -Gly-Cys-Met-Gly-Leu-Pro- (SEQ ID NO:37), -Gly-Cys-Met-Gly-Ser-Pro- (SEQ ID NO:38), -Gly-Lys-Lys-Lys-Ser-Gly- (SEQ ID NO:39), -Asn-Gly-Cys-Ile-Asn-Cys- (SEQ ID NO:40), -Asn-Lys-Arg-Arg-Arg-Gly- (SEQ ID NO:41), -Lys-Pro-Lys-Lys-Lys-Ser- (SEQ ID NO:42), -Ala-Arg-Lys-Lys-Ser-Ser- (SEQ ID NO:43), -Asp-Pro-Cys-Cys-Ser-Ala- (SEQ ID NO:44), -Lys-Lys-Arg-Lys-Arg-Lys- (SEQ ID NO:45), -Arg-Gln-Gln-Lys-Arg-Ala- (SEQ ID NO:46), -Lys-Arg-Ile-Arg-Glu-Arg- (SEQ ID NO:47), -Lys-Ser-Phe-Lys-Glu-Arg- (SEQ ID NO:48), -Gln-Pro-Thr-Arg-Asn-Gln- (SEQ ID NO:49), -Thr-Gln-Ser-Pro-Gln-Asn- (SEQ ID NO:50), -Ala-Pro-Ala-Pro-Gln-Cys- (SEQ ID NO:51), -Gln-Val-Ala-Pro-Gln-Asn- (SEQ ID NO:52), -Lys-Ser-Gly-Asn-Lys-Asn- (SEQ ID NO:53), -Arg-Ala-Trp-Asn-Lys-Ser- (SEQ ID NO:54), -Arg-Lys-Pro-Glu-Arg-Ser- (SEQ ID NO:55), -Arg-Thr-Thr-Ser-Arg-Gly- (SEQ ID NO:56), -Arg-Glu-Lys-Lys-Phe-Phe- (SEQ ID NO:57), -Lys-Glu-Leu-Lys-Gly-Gly- (SEQ ID NO:58), -Asp-Lys-Lys-Ser-Lys-Thr- (SEQ ID NO:59), -Gly-Pro-Ala-Ser-Lys-Ser- (SEQ ID NO:60) etc.

Pharmaceutically acceptable salts of compound (A) include acid-added salts, metal salts, organic base-added salts. Examples of pharmaceutically acceptable acid-added salts of compound (A) include salts with inorganic acids such as hydrochlorides, sulfates, phosphates, etc.; and salts with organic acids such as acetates, maleates, fumarates, tartrates, citrates, etc. Examples of pharmaceutically acceptable metal salts of compound (A) include alkali metal salts such as sodium salts, potassium salts, etc., alkaline earth metal salts such as magnesium salts, calcium salts, etc., as well as aluminium salts, zinc salts, etc. Examples of pharmaceutically acceptable organic bases include primary amines such as methylamine, ethylamine, aniline, etc., secondary amines such as dimethylamine, diethylamine; pyrrolidine, piperidine, morpholine, piperazine, etc., tertiary amines such as trimethylamine, triethylamine, N,N-dimethylaniline, pyridine, etc., and also ammonia, etc.

The abbreviations for amino acids and their protective groups referred to herein follow the recommendation of IUPAC-IUB Joint Commission on Biochemical Nomenclature (see Eur. J. Biochem., 138, 9 (1984)].

Unless otherwise specifically indicated; the following abbreviations are for the corresponding amino acids and protective groups.

Gly: glycine
Ala: L-alanine
Thr: L-threonine
Pro: L-proline
Asp: L-aspartic acid
Asn: L-asparagine
Asx: L-aspartic acid or L-asparagine
His: L-histidine
Tyr: L-tyrosine
Trp: L-tryptophan
Val: L-valine
Ser: L-serine
Leu: L-leucine
Ile: L-isoleucine
Met: L-methionine
Cys: L-cysteine
Phe: L-phenylalanine
Arg: L-arginine
D-Arg: D-arginine
D-Phe: D-phenylalanine
(N-Me)Ile: N-methyl-L-isoleucine Hyp: trans-4-hydroxy-L-proline
Fmoc: 9-fluorenylmethyloxycarbonyl
Boc: t-butyloxycarbonyl
t-Bu: t-butyl
Bzl: benzyl
CHO: formyl
Bom: benzyloxymethyl
Pmc: 2,2,5,7,8-pentamethylchroman-6-sulfonyl
Trt: trityl
Wang Resin: 4-(hydroxymethyl)phenoxymethyl-resin
Rink Amide MBHA Resin: 4-{2',4'-dimethoxyphenyl-(9-fluorenylmethyloxycarbonyl)-aminomethyl}-phenoxyacetamidonorleucyl-(4-methyl-benzhydryl-amine)-resin The following abbreviations are for the corresponding side-chain-protected amino acids mentioned below.

| | |
|---|---|
| Fmoc-Hyp(t-Bu)-OH: | $N^\alpha$-9-fluorenylmethyloxycarbonyl-O-t-butyl-trans-4-hydroxy-L-proline |
| Fmoc-His(Trt)-OH: | $N^\alpha$-9-fluorenylmethyloxycarbonyl-$N^{im}$-trityl-L-histidine |
| Fmoc-Asn(Trt)-OH: | $N^\alpha$-9-fluorenylmethyloxycarbonyl-$N^\gamma$-trityl-L-asparagine |
| Fmoc-Cys(Trt)-OH: | $N^\alpha$-9-fluorenylmethyloxycarbonyl-S-trityl-L-cysteine |
| Fmoc-(N-Me)Ile-OH: | $N^\alpha$-9-fluorenylmethyloxycarbonyl-N-methyl-L-isoleucine |
| Fmoc-Asp(Ot-Bu)-OH: | $N^\alpha$-9-fluorenylmethyloxy-carbonyl-L-aspartate-$\beta$-t-butyl |
| Fmoc-Tyr(t-Bu)-OH: | $N^\alpha$-9-fluorenylmethyloxycarbonyl-O-t-butyl-L-tyrosine |
| Fmoc-Thr(t-Bu)-OH: | $N^\alpha$-9-fluorenylmethyloxycarbonyl-O-t-butyl-L-threonine |
| Fmoc-Ser(t-Bu)-OH: | $N^\alpha$-9-fluorenylmethyloxycarbonyl-O-t-butyl-L-serine |
| Fmoc-Arg(Pmc)-OH: | $N^\alpha$-9-fluorenylmethyloxycarbonyl-N-2,2,5,7,8-pentamethylchroman-6-sulfonyl-L-arginine |
| Boc-Thr(Bzl)-OH: | $N^\alpha$-t-butyloxycarbonyl-O-benzyl-L-threonine |
| Boc-His(Bom)-OH: | $N^\alpha$-t-butyloxycarbonyl-$N^{im}$-benzyloxymethyl-L-histidine |
| Boc-Trp(CHO)-OH: | $N^\alpha$-t-butyloxycarbonyl-$N^{ind}$-formyl-L-tryptophan |
| H-Trp-OBzl: | L-tryptophanbenzyl ester |

The following abbreviations are for the corresponding reaction solvents and reagents mentioned below.
PyBOP: benzotriazol-1-yl-oxytripyrrolidinophosphonium hexafluorophosphate
HOBt: N-hydroxybenzotriazole
NMM: N-methylmorpholine
DCC: dicyclohexylcarbodiimide
HONSu: N-hydroxysuccinimide
DMF: N,N-dimethylformamide
TFA: trifluoroacetic acid
PBS: phosphoric acid-buffered saline
DCM: dichloromethane
DIEA: diisopropylcarbodiimide
DEPC: diethylphdsphoric acid cyanide
Pd/C: palladium/carbon catalyst
TCA: trichloroacetic acid
PMSF: phenylmethanesulfonyl fluoride
DMSO: N,N-dimethylsulfoxide
PyBroP: bromo-trispyrrolidinophosphonium hexafluorophosphate
DTT: dithiothreitol
SDS: sodium dodecylsulfate Methods for producing compound (A) are described below.

The cyclic peptide of compound (A) is obtained by producing peptides with suitably protected side chains by the use of a peptide synthesizer or according to conventional liquid-phase peptide synthesizing methods (see "Bases and Experiments for Synthesis of Peptides", Nobuo Izumiya et al., Maruzen Publishing), followed by cyclization in the presence of a condensing agent such as PyBOP or the like. The thus-prepared cyclic peptide is condensed with a C-terminal linear peptide, which is obtained by the use of a peptide synthesizer and/or according to a liquid-phase peptide producing method, thereby producing the intended compound (A).

Peptide synthesizers suitable for use include a peptide synthesizer produced by Applied Biosystems, Inc., U.S.A. (ABI) and a peptide synthesizer produced by Shimazu Seisakusho, Ltd. Using either of these synthesizers, intended peptides are produced in accordance with the manufacturer's instructions and starting from a suitable side-chain-protected $N^\alpha$-t-butyloxy-carbonylamino acid, etc. or a suitable side-chain-protected $N^\alpha$-9-fluorenylmethyloxy-carbonylamino acid, etc:

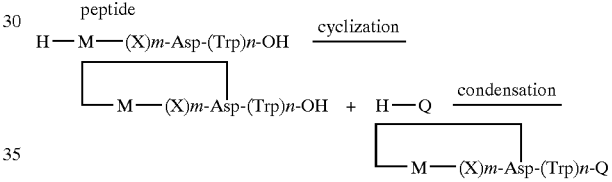

Protected amino acids which are the starting materials for producing compound (A) are available from ABI, Shimazu Seisakusho, Kokusan Chemical Co., Nova Biochem Co., Peptide Institute Inc. and Watanabe Chemical Industries Ltd.

The thus-obtained compound (A) can be purified by high-performance liquid chromatography (hereinafter referred to as HPLC) using a C-4, C-8 or C-18 reversed-phase silica gel column, or by column chromatography using any of partition or absorption resins, silica gel, chemically-modified silica gel, reversed-phase silica gel, alumina, diatomaceous earth, magnesium silicate, ion-exchanging resins, or gel filration, etc. or thin layer chromatography.

Pharmaceutically acceptable salts of compound (A) can be obtained by ordinary methods. More specifically, acid-added salts and organic base-added salts of compound (A) can be obtained by dissolving compound (A) in an aqueous solution of the corresponding acid or organic base, followed by freeze-drying the resulting solution. Metal salts of compound (A) can be obtained by dissolving compound (A) in an aqueous solution containing the corresponding metal ions, followed by purifying the resulting salt by gel filtration or HPLC.

Specific examples of compound (A) are shown in Table 1 below.

TABLE 1

| Compound No. | Physiologically active peptide | Sequence length | Sequence |
|---|---|---|---|
| 1 | I | 19 | Gly-Asn-Trp-His-Gly-Thr-Ala-Pro-Asp-Trp-Val-Thr-Gly-Arg-Gly-Asp-Ser-Pro-Ala-OH |
| 2 | I | 22 | Gly-Asn-Trp-His-Gly-Thr-Ala-Pro-Asp-Trp-Val-Tyr-Ala-Val-Thr-Gly-Arg-Gly-Asp-Ser-Pro-Ala-NH$_2$ |
| 3 | II | 19 | Gly-Asn-Trp-His-Gly-Thr-Ala-Pro-Asp-Trp-Ser-Met-Gly-Leu-Pro-Cys-Val-Val-Met-OH |
| 4 | II | 17 | Gly-Asn-Trp-His-Gly-Thr-Ala-Pro-Asp-Trp-Ser-Ser-Gly-Cys-Val-Leu-Ser-OH |
| 5 | II | 19 | Gly-Asn-Trp-His-Gly-Thr-Ala-Pro-Asp-Trp-Ser-Met-Gly-Leu-Pro-Cys-Ile-Phe-Met-OH |
| *6 | III | 18 | Gly-Asn-Trp-His-Gly-Thr-Ala-Pro-Asp-Trp-Phe-Gly-Gly-Arg-Ile-Asp-Arg-Ile-NH$_2$ |
| 7 | III | 22 | Gly-Asn-Trp-His-Gly-Thr-Ala-Pro-Asp-Trp-Ala-Phe-Gly-Gly-Arg-Ile-Asp-Arg-Ile-Gly-Ala-Ala-NH$_2$ |
| 8 | III | 18 | Gly-Asn-Trp-His-Gly-Thr-Ala-Pro-Asp-Trp-Phe-Gly-Gly-D-Arg-Ile-Asp-Arg-Ile-NH$_2$ |
| 9 | III | 18 | Gly-Asn-Trp-His-Gly-Thr-Ala-Pro-Asp-Trp-Phe-Gly-Gly-D-Arg-Ile-Asp-D-Arg-Ile-NH$_2$ |
| 10 | III | 18 | Gly-Asn-Trp-His-Gly-Thr-Ala-Pro-Asp-Trp-Phe-Gly-Gly-Arg-(N-Me)Ile-Asp-Arg-Ile-NH$_2$ |
| 11 | IV | 20 | Gly-Asn-Trp-His-Gly-Thr-Ala-Pro-Asp-Trp-D-Arg-Arg-Pro-IIyp-Gly-Phe-Ser-D-Phe-Leu-Arg-OH |

The physiological activities of compound (A) and the stability thereof against protease are described below.

Test Example 1: Physiological Activities
(1) Cell-adhesion Inhibiting Activity

To a 96-well flat bottom plate (Sumitomo Bakelite Co.) added were 50 μg/well (5 μg/ml-culture) of mouse fibronectin (produced by Telios Pharmaceutical Inc.). The plate was allowed to stand for 2 hours at room temperature to coat with mouse fibronectin. A test compound, compound (1) or compound (b) was dissolved in PBS at varying concentrations shown in FIG. 1. Each solution was added to the plate. Next, biotin-labeled B16-F10 (mouse melanoma) cells were added thereto and incubated at 37° C. for 30 minutes. After incubation, the non-adhered cells were removed by suction, and the adhered cells were fixed by 0.25% glutaraldehyde/PBS. The thus-fixed cells were washed with Tween-PBS, and peroxidase-labeled avidin D (Vector Co.) was added thereto and reacted for one hour at room temperature. Thereafter, the cells were washed with Tween-PBS and colored with an ABTS solution. Using NJ-2001 (Nippon Intermed Co.), the absorbance of the colored cells at OD415 was measured by colorimetry.

From the absorbance thus measured, the percentage inhibition of adhesion of the cells was obtained according to the following equation:

Percentage Inhibition of Cell Adhesion=$[(A-B)/A]\times 100$

A: absorbance in the absence of the test compound
B: absorbance in the presence of the test compound The non-adhered cells was washed out using an Eppendorf pipette (through which culture medium was applied to the cells to wash them, since the cells were not fixed) and a suction device equipped with a 18-G injector needle at its tip. (The non-adhered cells were removed by 3 to 5 repetitions of suction.) The other washing operations were effected by injection with an Eppendorf pipette and decantation.

The labeling of cells with biotin was conducted according to the following method.

From 0.2 to 0.5 mg of NHS-LC-biotin (Pierce Co.) were dissolved in 1 ml of PBS, and the resulting solution was mixed with blood cells ($1\times 10^7$ to $2\times 10^7$ cells/ml-culture medium). The cells were then incubated at room temperature for 30 minutes. After the reaction, the culture was washed three times each with PBS to remove the unlabeled biotin. Thus, biotin-labeled mouse melanoma cells were prepared.

The results obtained are shown in FIG. 1. The concentration of compound (b) for 50% inhibition of the adhesion of the cells ($IC_{50}$) was 1130 $\mu$M, while that of compound (1) for $IC_{50}$ was 290 $\mu$M.

The same test was applied to compound (2) and compound (c). The results are shown in FIG. 2. Both compounds showed almost the same cell adhesion-inhibiting activity.

(2). Inhibitory Activity Against Agglutination of Platelets Stimulated by Collagen The blood was collected from the heart of a white rabbit (male weight 2 kg) and mixed with 3.8% sodium citrate (1:9 3.8% sodium citrate/blood). The mixture was centrifuged at 900 r.p.m., and the supernatant was isolated as platelet-rich plasma (PRP). The remaining lower layer was centrifuged at 2500 r.p.m., and the supernatent was isolated as platelet-poor plasma (PPP). These isolates were used in the following test. The percentage of platelet agglutination was measured, using a platelet agglutination measuring device, TE-500 (produced by Elmer Optical Co.). As the standard for platelet agglutination in this test, the percentage of platelet agglutination measured in PRP only was defined as 0%, while that measured in PPP only as 100%. Test solutions each containing a test compound, compound (1) or compound (b) were prepared so as to give a final concentration of 1, 0.3 or 0.1 mM.

Ten $\mu$l of re-distilled water (as a control) or the test solution and 200 $\mu$l of PRP were put into a cuvet and pre-incubated for 3 minutes, then 10 $\mu$l of a collagen that had been prepared to have a final concentration of 10 $\mu$g/ml were added thereto, and the percentage of platelet agglutination was measured. The results obtained are shown in Table 2.

TABLE 2

| Test compound | Concentration of test compound (mM) | Percentage of platelet agglutination inhibition (%) |
|---|---|---|
| Compound 1 | 0.1 | 28.3 |
|  | 0.3 | 78.4 |
|  | 1.0 | 92.1 |
| Compound b | 0.3 | 20.3 |
|  | 1.0 | 61.2 |

(3) Protein-farnesyltransferase-inhibiting Activity (1) in a System Containing Ras Protein as the Substrate Using a protein-farnesyltransferase derived from bovine brains, the amount of [hu 3H]-farnesyl diphosphate (20 Ci/mmol, Amersham Co.) that had been transferred to Ras protein (v-Ki-Ras p21) was determined by measuring the amount of the radiation from the reaction system with a liquid scintillation counter. Fifty $\mu$l of a reaction liquid was prepared, comprising v-Ki-Ras p21 (2 $\mu$g), [$^3$H]-farnesyl diphosphate (0.1 $\mu$M), 50 mM Tris-HCl (pH 7.5), 20 mM KCl, 10 mM MgCl$_2$, 5 mMDTT, protein-farnesyltransferase (1.5 $\mu$g) that had been prepared by the method mentioned below, and a test compound (5 $\mu$l, as a DMSO solution). Specifically, a reaction liquid comprising all the above-mentioned components, except [$^3$H]-farnesyl diphosphate, was pre-incubated at 37° C. for 3 minutes, and thereafter [$^3$H]-farnesyl diphosphate was added thereto to start the reaction. After reaction at 37° C. for 30 minutes, 0.5 ml of 4% SDS were added to the reaction mixture to stop the reaction. Next, 0.5 ml. of 30% TCA were added thereto, and the reaction mixture was allowed to stand on ice for 60 minutes. The denatured protein was adsorbed onto a glass filter (Whattman GF/C, 2.4 cm) by suction filtration (using Advantec Multi Filter MF12G). The container used for the reaction was washed twice each with 2 ml of 2% SDS/5% TCA, and the glass filter used was washed five times each with 2 ml of 6% TCA. These washings were dried for 30 minutes and mixed with 6 ml of a scintillation liquid. The amount of radiation was measured with a liquid scintillation counter.

From the amount thus measured, the percentage inhibition of the enzyme was calculated according to the following equation:

Percentage inhibition=$[(A-B)/A]\times 100$

A: Radioactivity of the filter in the absence of the test compound
B: Radioactivity of the filter in the presence of the test compound V-Ki-Ras p21, which was used as the substrate for the assay, was prepared by allowing *Escherichia coli* to express the protein in the form of granules, solubilizing it with 3.5 M guanidine hydrochloride, 50; mM Tris-HCl (pH 7.5) and 1 mM ethylenediaminetetraacetic acid (EDTA), and purifying it according to the method of Hara et al [Oncogene Research, 2, 325–33.3 (1988)]0 to serve as a substrate.

The protein-farnesyltransferase used in the assay was prepared from bovine brain, according to the method described below (J. Biol. Chem., 266, 14603–10 (1991)].

Three hundred g of bovine brain were homogenized in 2 liters of a buffer containing 50 mM Tris-HCl (pH 8.0), 1 mM EDTA, 1 mM MgCl$_2$, 5 mM DTT, 2 $\mu$g/ml of leupeptin, 2

μg/ml of antipain and 0.2 mM PMSF, and centrifuged for 1 hour at 10,000×g. The resulting supernatant was further centrifuged for 2 hours at 33,000×g. The supernatant thus separated was passed through a DEAE-Sephacel column (column capacity: 500 ml) that had been previously equilibrated with the above-described buffer. Afterwards, the column was washed with the same buffer and subjected to linear gradient elution (0 to 500 mM NaCl) using 1 liter of the same buffer and 1 liter of the same buffer with 500 MM NaCl as an eluent. The enzymatic activity of each eluate fraction was measured, and the enzymatically active fractions were concentrated. The resulting concentrate was subjected to dialysis against a buffer containing 20 mM Tris-HCl (pH 8.0), 50 mM NaCl, 20 mM $ZnCl_2$ and 0.2 mM PMSF. The thus-obtained partially purified enzyme was used in the assay. The results are shown in Table 3.

TABLE 3

| Test compound | *$IC_{50}$ (μM) | Test compound | *$IC_{50}$ (μM) |
|---|---|---|---|
| Compound 3 | 0.56 | Compound d | 1.6 |
| Compound 4 | 9 | Compound e | 10 |
| Compound 5 | 19 | Compound f | 21 |

*Concentration of the test compound which inhibits 50% of the enzymatic activity.

(4) Protein-farnesyltransferase Inhibiting Activity (2) in SPA Enzyme Assay Kit

Using a farnesyltransferase [hu 3H]-SPA enzyme assay kit (Amersham Co.) and the same protein-farnesyltransferase as employed in Test Example 1(3), the intake of [$^3$H]-farnesyl diphosphate by biotin-lamin-B peptide was measured. The kit was utilized in accordance with the manufacturer's instructions. In the same manner as in Test Example 1(3), the percentage inhibition of the enzyme was calculated. The results obtained are shown in Table 4.

TABLE 4

| Test compound | *$IC_{50}$ (μM) | Test compound | *$IC_{50}$ (μM) |
|---|---|---|---|
| Compound 3 | 0.42 | Compound d | 1.2 |

*Concentration of the test compound which inhibits 50% of the enzymatic activity.

(5) Inhibitory Activity Against Binding of ANP to Bovine Lung-derived ANP Receptor Using a polytron (Type PT10/35, produced by Kinematica Gmbh), bovine lung tissue was homogenized in buffer (A) (comprising 1 mM $NaHCO_3$, 5 mM EDTA, 5 μg/ml of leupeptin, 5 μg/ml of pepstatin A, 40 μM PMSF, pH 8.3) at 4° C.

The suspension thus obtained was centrifuged at 4° C. for 10 minutes at 8,000×g to obtain the supernatant. The resulting supernatant was further centrifuged at 4° C. for 60 minutes at 40,000×g, and the solid was collected. The solid was suspended in buffer (A), and the resulting suspension was centrifuged at 4° C. for 60 minutes at 40,000×g. The solid thus separated was suspended to give a protein content of 2 mg/ml to serve as a membrane fraction.

A 12.5 μl portion of the suspension was added to 1 ml of buffer (B) (containing 50 mM Tris-HCl, 1 mM EDTA, 0.2% bovine serum albumin, pH 7.6) to prepare a membrane fraction solution.

$^{125}$I-rat ANP (about 30,000 cpm) was added to each of the membrane fraction solutions, to which non-labeled rat ANP (final concentration: 1 μM) had been added, a test compound had been added or none of these had been added. These mixtures were separately incubated at 25° C. for 2 hours.

Each of the thus-incubated mixtures was filtered through a glass filter, GF/B (Whattman Co.) that had been previously dipped in 0.3% polyethyleneimine. The filter was washed with buffer (C) (comprising 50 mM Tris-HCl, 1 mM EDTA, pH 7.6), and the radioactivity of the filter was measured to determine the amount of the $^{123}$I-rat ANP bound to the receptor and non-specifically bound $^{125}$I-rat ANP. The percentage inhibition of rat ANP-receptor binding was calculated according to the following equation:

Percentage inhibition=[(C−A)/(C−B)]×100

A: Radioactivity in the presence of the test compound

B: Radioactivity in the presence of the non-labeled rat ANP

C: Radioactivity in the absence of both the test compound and the non-labeled rat ANP The results are shown in Table 5.

TABLE 5

| Test compound | *$IC_{50}$ (nM) | Test compound | *$IC_{50}$ (nM) |
|---|---|---|---|
| Compound 6 | 0.34 | Compound g | 3.5 |
| Compound 7 | 1.7 | Compound h | 2.5 |
| Compound 8 | 5.9 | Compound i | 210 |
| Compound 9 | 290 | Compound j | 5400 |
| Compound 10 | 1.5 | Compound k | 21 |

*Concentration of the test compound which inhibits 50% of the binding activity of $^{125}$I-ANP to the receptor.

(6) BK-receptor Binding Inhibiting Activity

Inhibition of the binding of BK to the BK receptor derived from guinea pig ilea

Using a polytron (Type PT10/35, Kinematica Gmbh), guinea pig ilea was homogenized in buffer (A) (containing 25 mM N-tris(hydroxymethyl)methyl-2-aminoethane-sulfonic acid-NaOH, pH 6.8) at 4° C.

The suspension thus obtained was centrifuged at 4° C. for 10 minutes at 8,000×g, and the supernatant was collected. The supernatant was further centrifuged at 4° C. for 60 minutes at 40,000×g, and the solid was collected. The solid was suspended in buffer (A), and the resulting suspension was centrifuged at 4° C. for 60 minutes at 40,000×g. The resulting solid was suspended to give a protein content of 2 mg/ml to serve as a membrane fraction.

A 12.5 μl portion of the suspension were added to 1 ml of buffer (B) (containing 25 mM N-tris(:hydroxymethyl) methyl-2-aminoethanesulfonic acid-NaOH, 0.1% bovine serum albumin, 0.014% bacitracin, pH 6.8) to prepare a membrane fraction solution.

$^3$H-BK (200 pM) was added to each of the membrane fraction solutions, to which non-labeled BK (final concentration: 1 μM) had been added, a test compound had been added or none of these had been added. These mixtures were separately incubated at 25° C. for 1.5 hours. Each of the thus-incubated mixtures was filtered through a glass filter, GF/B (Whattman Co.) that had been previously dipped in 0.3% polyethyleneimine. The filter was washed with buffer (C) (comprising 50 mM Tris-HCl, 1 mM EDTA, pH 7.6), and the radioactivity of the filter was measured, using a liquid scintillation counter (LSC3500, Aroka Co.) to determine the amount of the $^3$H-BK bound to the receptor and non-specifically bound 3H-BK. The percentage inhibition of the guinea pig-derived BK receptor binding activity was calculated according to the following equation:

Percentage inhibition=$[(C-A)/(C-B)]\times 100$

A: Radioactivity in the presence of the test compound
B: Radioactivity in the presence of the non-labeled BK
C: Radioactivity in the absence of both the test compound and the non-labeled BK The results obtained are shown in Table 6.

TABLE 6

| Test compound | Concentration of test compound added (M) | Percentage inhibition (%) |
|---|---|---|
| Compound 11 | $10^{-8}$ | 46 |
|  | $10^{-7}$ | 85 |
| Compound m | $10^{-8}$ | 20 |
|  | $10^{-7}$ | 68 |

TEST EXAMPLE 2

Stability to Trypsin

Compound (1) or compound (b) was dissolved in a PBS(−) buffer (pH 7.2) containing 0.01% sodium azide and 0.1 mM calcium chloride to give a concentration of the compound of 25 μg/ml. To this was added trypsin (Sigma Co.) in an amount of 1/20 weight of compound (1) or (b). The resulting solution was incubated at 37° C. and sampled at intervals. The samples were analyzed by HPLC, using a reversed-phase column (YMC-Pack, ODS-AM, 150×6 mm I.D.). Elution was carried out by linear gradient elution using acetonitrile (0% to 45%) containing 0.1% TFA for 30 minutes. Absorbance at 220 nm of the eluates was measured.

From the values obtained at intervals, the residual amount of compound (1) or (b) was calculated as a relative value based on the height of the peak for compound (1) or (b) not treated with trypsin which was regarded as 100% The results are shown in FIG. 3. The half-life of compound (b) was shorter than 2 hours, while about 60% of compound (1) still remained after 9 hours.

TEST EXAMPLE 3

Stability to α-chymotrypsin

Compound (2) or compound (c) was dissolved in a PBS(−) buffer (pH 7.2) containing 0.01% sodium azide and 0.1 mM calcium chloride to give a concentration of the compound of 25 μg/ml. To this were added α-chymotrypsin (Sigma Co.) and $N^\alpha$-p-tosyl-L-lysine chloromethyl ketone (Sigma Co.) each in an amount of 1/10 weight of compound (2) or (c). The resulting mixture was incubated at 37° C. and sampled at intervals. The samples were analyzed by HPLC, using a reversed-phase column (YMC-Pack, ODS-AM, 150×6 mm I.D.). Elution was carried out by linear gradient elution using acetonitrile (0% to 45%) containing 0.1% TFA for 30 minutes. Absorbance at 220 nm of the eluate was measured.

From the values obtained at intervals, the residual amount of compound (2) or (c) was calculated as a relative value based on the height of the peak for compound (2) or (c) not treated with α-chymotrypsin, which was regarded as 100%. The results are shown in FIG. 4. The half-life of compound (c) was shorter than 1 hour, while about 95% of compound (2) still remained after 6 hours.

TEST EXAMPLE 4

Stability to Prolyl-endopeptidase

Compound (3) or compound (d) was dissolved in a PBS(−) buffer (pH 7.2) containing 0.01% sodium azide, 0.1 mM calcium chloride and 0.5 mM DTT to give a concentration of the compound of 25 μg/ml. To this was added prolyl-endopeptidase (Seikagaku Corporation) in an amount of 1/500 weight of compound (3) or (d). The resulting mixture was incubated at 37° C. and sampled at intervals. The samples were analyzed by HPLC, using a reversed-phase column (YMC-Pack, ODS-AM, 150×6 mm I.D.). Elution was carried out by linear gradient elution using acetonitrile (0% to 45%) containing 0.1% TFA for 30 minutes. Absorbance at 220 nm of the eluate was measured.

As to the values obtained at intervals, the residual amount of compound (3) or (d) was calculated as a relative value based on the height of the peak for compound (3) or (d) not treated with prolyl-endopeptidase, which was regarded as 100%. The results are shown in FIG. 5. The half-life of compound (d) was shorter than 1 hour, while about 60% of compound (3) still remained after 7 hours.

Compound (5) and compound (f) were tested in the same manner as above, and the results obtained are shown in FIG. 6. Only 12% of compound (f) remained after 1 hour, while 63% of compound (5) remained.

BEST MODES FOR PRACTICE OF THE INVENTION

Figure 1:
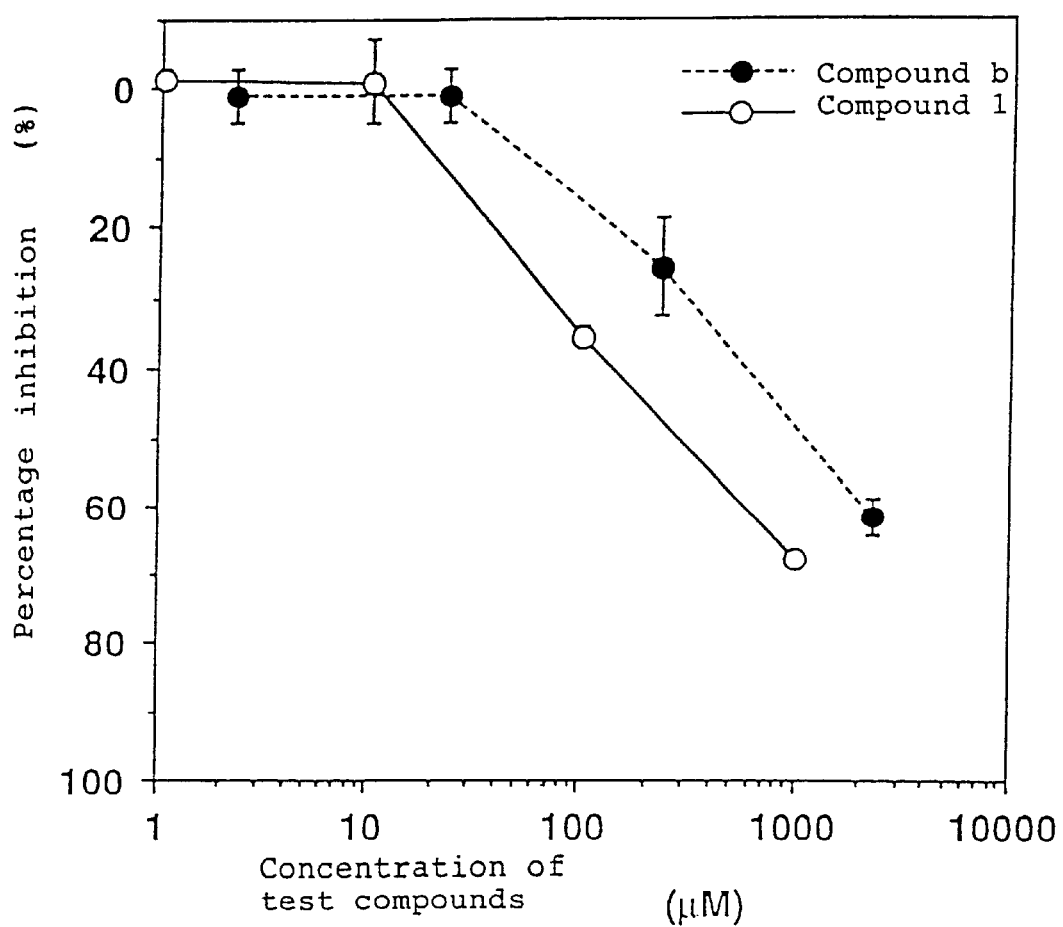
FIG. 1 shows the percentages inhibition of cell adhesion by compound (1) and compound (b) at varying concentrations of the compounds.
Figure 2:
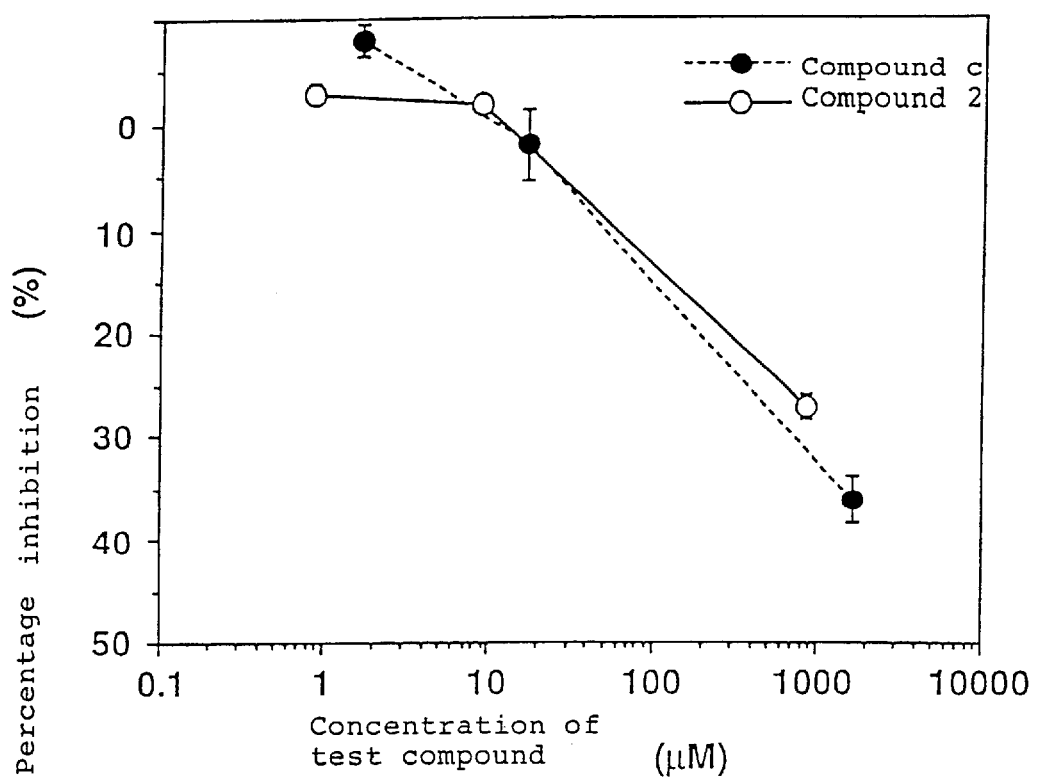
FIG. 2 shows the percentages inhibition of cell adhesion by compound (2) and compound (c) at varying concentrations of the compounds.
Figure 3:
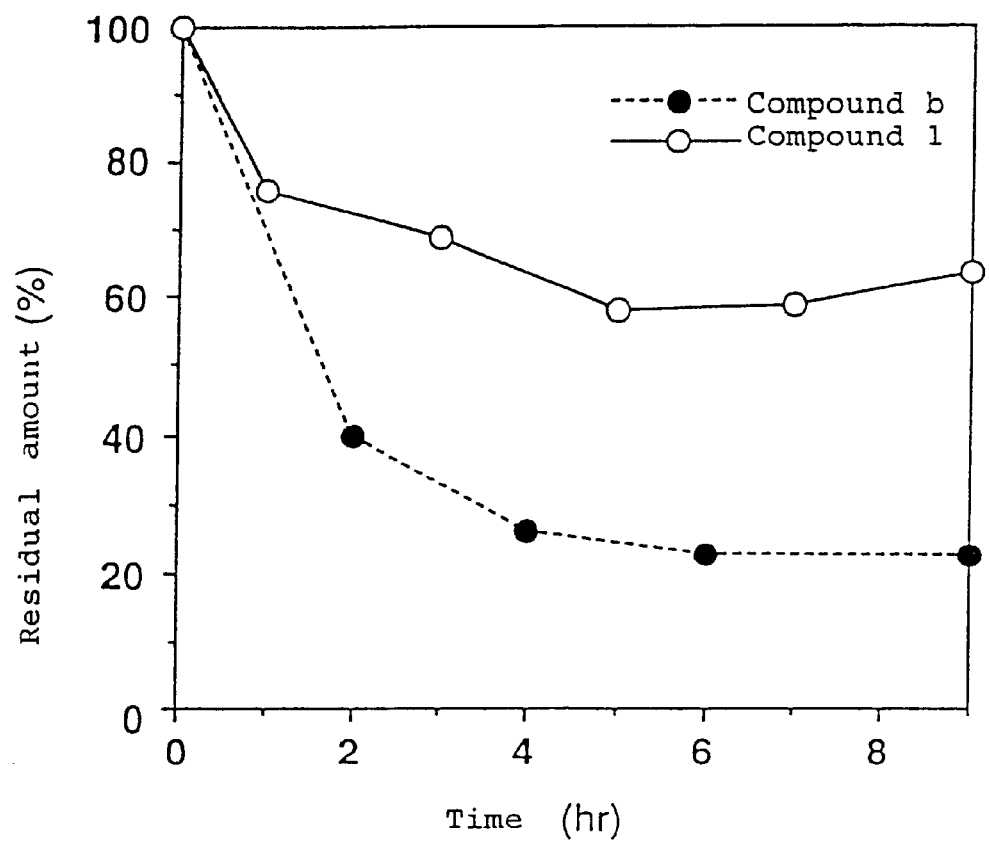
FIG. 3 indicates the stability of compound (1) and compound (b) to trypsin in terms of the percent remaining per unit time.
Figure 4:
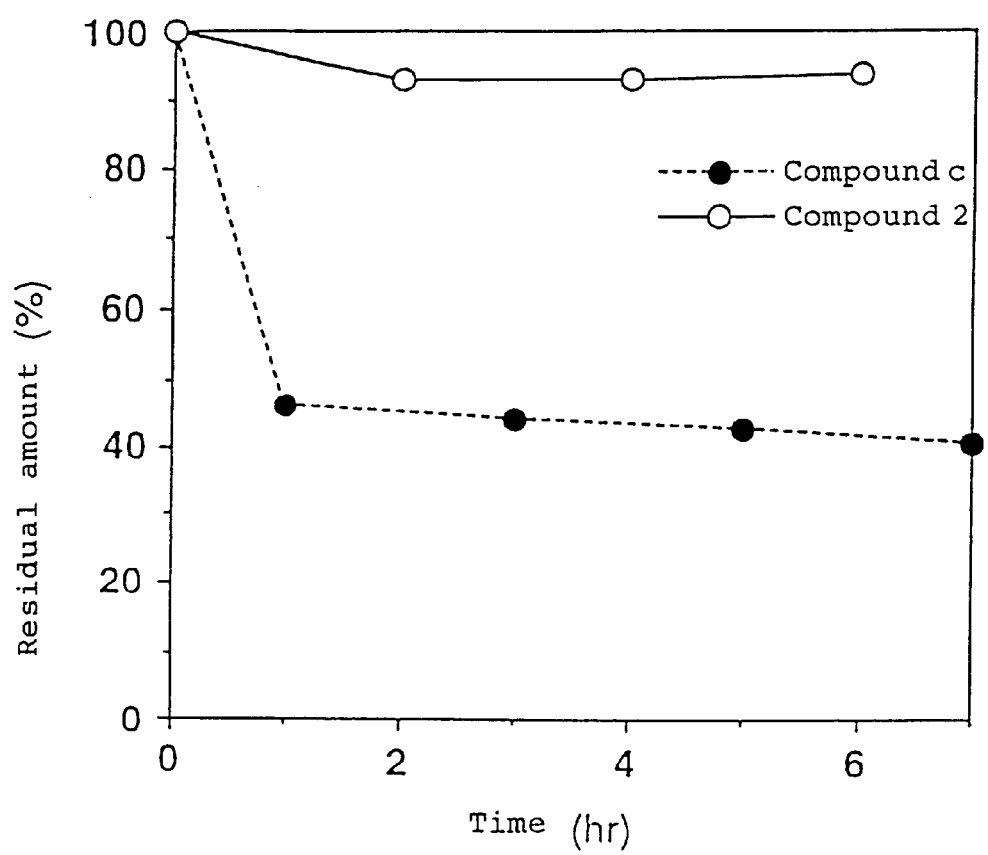
FIG. 4 indicates the stability of compound (2) and compound (c) to α-chymotrypsin in terms of the percent remaining per unit time.
Figure 5:
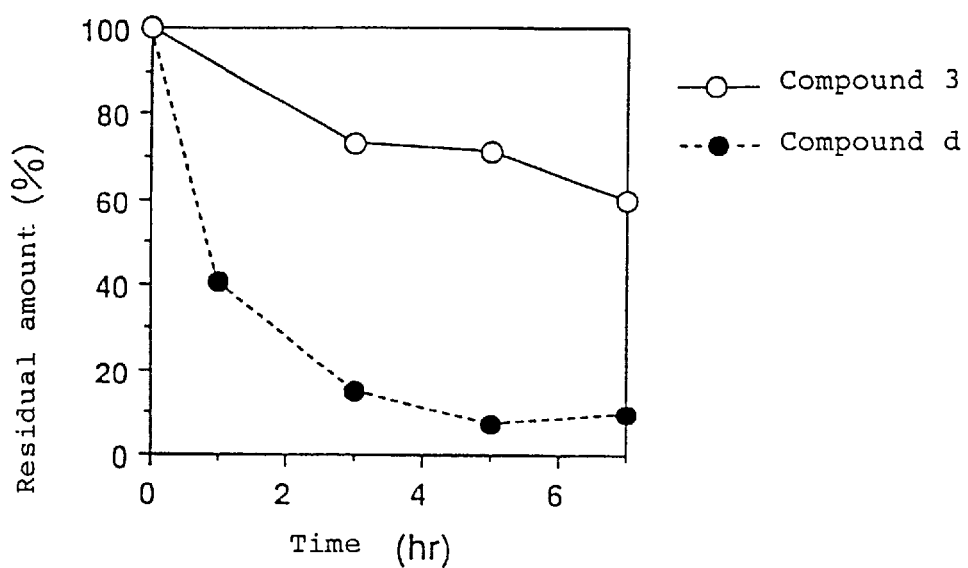
FIG. 5 indicates the stability of compound (3) and compound. (d) to prolyl-endopeptidase in terms of the percent remaining per unit time.
Figure 6:
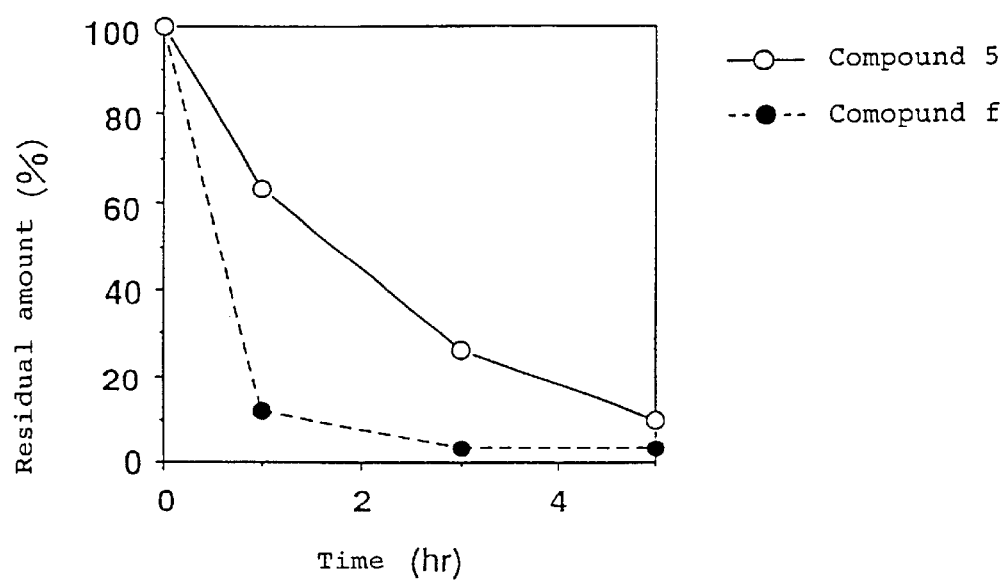
FIG. 6 indicates the stability of compound (5) and compound (f) to prolyl-endopeptidase in terms of the percent remaining per unit time.

In the following examples, the physicochemical properties, of the compounds were measured with the following instruments.

Mass spectra: JEOL JMS-SX102A (measured by the FAB method).

The amino acid analysis were carried out according to the method of Bidlingmeyer, B. A. et al. [J. Chromatogr., 336, 93 (1984)]. Hydrolysis was carried out in hydrochloric acid vapor at 110° C. for 22 hours. The amino acid composition of the resulting hydrolyzates were analyzed with Waters Pico Tag amino acid analyzer. The measured values are shown as taking the value for Ala as 1.00

EXAMPLE 1

Synthesis of Compound (1)

A 3.4 mg-portion of compound (a) obtained in Reference Example 1 was dissolved in 0.49 ml of DMF, and 3.1 mg of PyBOP, 0.8 mg of HOBt and 0.99 µl of NMM were added thereto while cooling on ice. The resulting mixture was allowed to stand for 20 minutes, still while cooling on ice. Twenty-five mg of the peptide-bonded carrier resin obtained in Reference Example 2 were added thereto and stirred at 4° C. for 21 hours. The carrier resin was collected by filtration, washed with methanol and butyl ether and dried for 1 hour under reduced pressure. To the thus-obtained resin added were 150 µl of a mixed solution containing, 82.5% TFA, 5% thioanisole, 5% water, 3% ethylmethyl sulfide, 2.5% 1,2-ethanedithiol and 2% thiophenol and supplemented with 5 mg/ml of 2-methylindole. This was allowed to stand at room temperature for 7 hours in order to remove the side-chain-protecting groups and cleave the peptide from the resin. The resin was removed by filtration. About 10 ml of ether were added to the filtrate, and the precipitate formed was collected as a crude peptide. This was purified by HPLC in the same manner as in Reference Example 2 to obtain 0.9 mg of compound (1).

Mass Analysis [FABMS]: 1962 (M+H).

Amino Acid Analysis: Asx 2.9 (3), Gly 4.8 (4), Thr 1.9 (2), Ala 2.0 (2), Pro 1.9 (2), Val 1.0 (1), His 0.8 (1), Arg 1.1 (1), Ser 1.4 (1), Trp (not determined).

EXAMPLE 2

Synthesis of Compound (2)

A 2.24 mg portion of compound (a) obtained in Reference Example 1 was dissolved in 1 ml of DMF, and 10 µl of a DMF solution containing 1.04 mg of PyBOP, 10 µl of a DMF solution containing 0.27 mg of HOBt and 10 µl of a DMF solution containing 0.22 µl of NMM were added thereto while cooling on ice. This was allowed to stand for 15 minutes still while cooling on ice and then for 10 minutes at room temperature. This solution was again cooled on ice, and 0.5 ml of a DMF solution containing 3.57 mg of compound (c) obtained in Reference Example 3 were added thereto. The resulting mixture was stirred at 4° C. for 16 hours and at room temperature for 3 hours. This was again cooled on ice and the same amount of the DMF solutions each containing PyBOP, HOBt and NMM as described above was added thereto. The resulting mixture was allowed to stand for 30 minutes while cooling on ice. After further adding 3.57 mg of compound (c) thereto, the mixture was stirred at 4° C. for 51 hours and at room temperature for 4 hours. The mixture was neutralized with 2 M acetic acid and then purified by HPLC in the same manner as in Reference Example 2 to obtain 3.0 mg of compound (2).

Mass Analysis [FABMS]: 2294 (M+H).

Amino Acid Analysis: Asx 2.4 (3), Gly 4.2 (4), Thr 1.9 (2), Ala 3.0 (3), Pro 1.9 (2), Val 1.8 (2), His 1.0 (1), Arg 1.0 (1), Ser 0.9 (1), Tyr 0.9 (1), Trp (not determined).

EXAMPLE 3

Synthesis of Compound (3)

A 5.6 mg portion of compound (a) obtained in Reference Example 1 was dissolved in 0.91 ml of DMF, and 5.3 mg of PYBOP, 1.4 mg of HOBt and 1.6 µl of NMM were added thereto while cooling on ice. The resulting mixture was allowed to stand for, 20 minutes, still while cooling on ice. Forty mg of the peptide-bonded carrier resin obtained in Reference Example 4 were added thereto and stirred at 4° C. for 24 hours. The carrier resin was collected by filtration, washed with methanol and butyl ether and dried for 1 hour under reduced pressure. To the thus-obtained resin were added 200 µl of a mixed solution containing 90% TFA, 5% thioanisole and 5% 1,2-ethanedithiol and supplemented with 5 mg/ml of 2-methylindole. The mixture was allowed to stand at room temperature for, 2 hours in order to remove the side-chain-protecting groups and cleave the peptide from the resin. The resin was removed by filtration, about 2 ml of ether were added to the filtrate, and the precipitate formed was collected as a crude peptide. This was purified by HPLC in the same manner as in Reference Example 2 to obtain 0.24 mg of compound (3).

Mass Analysis [FABMS]: 2039 (M+H).

Amino Acid Analysis: Asx 1.2 (2), Gly 3.0 (3), Thr 1.0 (1), Ala 0.9 (1), Pro 1.7 (2), Val 1.3 (2), His 0.9 (1), Met 1.7 (2), Ser 1.1 (1), Leu 1.0 (1), Cys and Trp (not determined).

EXAMPLE 4

Synthesis of Compound (4)

A 3.5 mg portion of compound (a) obtained in Reference Example 1 was dissolved in 0.95 ml of DMF, and 3.3 mg of PyBOP, 0.9 mg of HOBt and 1.0 µl of NMM were added thereto while cooling on ice. This was allowed to stand for 1 hour still while cooling on ice. A 15.1 mg portion of the peptide-bonded carrier resin obtained in Reference Example 5 was added thereto and stirred at 4° C. for 24 hours. The carrier resin was collected by filtration, and washing, drying, cleavage of the peptide and purification by HPLC were carried out in the same manner as in Example 3. Thus, 1.9 mg of compound (4) were obtained.

Mass Analysis [FABMS]: 1755 (M+H).

Amino Acid Analysis: Asx 0.6 (2), Gly 2.7 (3), Thr 0.8 (1), Ala 0.9 (1), Pro 0.9 (1), Val 0.8 (1), His 0.7 (1), Leu 1.0 (1), Ser 2.5 (3), Cys and Trp (not determined).

EXAMPLE 5

Synthesis of Compound (5)

A 9.71 mg portion of compound (a) obtained in Reference Example 1 was dissolved in 0.76 ml of DMF, and 9.0 mg of PyBOP, 2.65 mg of HOBt and 2.85 µl of NMM were added thereto while cooling on ice. The resulting mixture was allowed to stand for 20 minutes still while cooling on ice. A 40.3 mg portion of the peptide-bonded carrier resin obtained in Reference Example 6 was added thereto and stirred at 4° C. for 24 hours. The carrier resin was collected by filtration, and washing, drying, cleavage of the peptide and purification by HPLC were carried out in the same manner as in Example 3. Thus, 8.9 mg of compound (5) were obtained.

Mass Analysis [FABMS]: 2101 (M+H).

Amino Acid Analysis: Asx 1.3 (2), Ser 1.1 (1), Gly 3.2 (3), His 0.9 (1), Ala 1.0 (1), Pro 2.1 (2), Met 2.0 (2), Ile 0.9 (1), Leu 1.2 (1), Phe 1.0 (1), Trp and Cys (not determined).

EXAMPLE 6

Synthesis of Compound (6)

A 4.0 mg portion of compound (a) obtained in Reference Example 1 was dissolved in 0.65 ml of DMF, and 3.7 mg of PyBOP, 1.0 mg of HOBt and 1.2 µl of NMM were added thereto while cooling on ice. The resulting mixture was allowed to stand for 20 minutes, still while cooling on ice. A 43.1 mg portion of the peptide-bonded carrier resin obtained in Reference Example 7 was added thereto and stirred at 4° C. for 24 hours. The carrier resin was collected by filtration, washed with methanol and butyl ether and dried for 1 hour under reduced pressure. To the thus-obtained resin were added 200 µl of a mixed solution containing 82.5% TFA, 5% water, 5% thioanisole, 2.5% 1,2-ethanedithiol, 3% ethylmethyl sulfide and 2% thiophenol and supplemented with 5 mg/ml of 2-methylindole. The resulting mixture was allowed to stand at room temperature for 6 hours in order to remove the side-chain-protecting groups and cleave the peptide from the resin. The resin was removed by filtration, about 2 ml of ether were added to the filtrate, and the precipitate formed was collected as a crude peptide. The peptide was purified by HPLC in the same manner as in Reference Example 2 to obtain 1.3 mg of compound (6).

Mass Analysis [FABMS]: 2035 (M+H).

Amino Acid Analysis: Asx 1.6 (3), Gly 3.8 (4), His 0.9 (1), Arg 1.7 (2), Thr 1.0 (1), Ala 1.0 (1), Pro 0.9 (1), Ile 1.8 (2), Phe 0.8 (1), Trp (not determined).

EXAMPLE 7

Synthesis of Compound (7)

A 3.8 mg portion of compound (a) obtained in Reference Example 1 was dissolved in 0.62 ml of DMF, and 3.5 mg of PyBOP, 0.9 mg of HOBt and 1.1 µl of NMM were added thereto while cooling on ice. The resulting solution was allowed to stand for 20 minutes still while cooling on ice. A 48.9 mg portion of the peptide-bonded carrier resin obtained in Reference Example 8 was added thereto and stirred at 4° C. for 24 hours and then at room temperature for 24 hours. The carrier resin was collected by filtration and 1.8 mg of PyBOP, 0.5 mg of HOBt and 0.4 µl of NMM were added to the filtrate while cooling on ice. The resulting mixture was allowed to stand for 2 hours still while cooling on ice. The carrier resin that had been collected by filtration was added to the mixture and then stirred at 4° C. for 24 hours. Then, the carrier resin was collected by filtration and washing, drying, cleavage of the peptide and purification by HPLC were carried out in the same manner as in Example 6. Thus, 1.3. mg of compound (7) were obtained.

Mass Analysis [FABMS]: 2305 (M+H).

Amino Acid Analysis: Asx 2.3 (3), Gly 5.3 (5), His 0.9 (1), Arg 1.9 (2), Thr 1.0 (1), Ala 4.0 (4), Pro 1.0 (1), Ile 2.0 (2), Phe 1.0 (1), Trp (not determined).

EXAMPLE 8

Synthesis of Compound (8)

A 1.0 mg portion of compound (a) obtained in Reference Example 1 were dissolved in 0.22 ml of DMF, and 0.94 mg of PyBOP, 0.24 mg of HOBt and 0.3 µl of NMM were added thereto while cooling on ice. The resulting mixture was allowed to stand for 20 minutes still while cooling on ice. A 3.53 mg portion of the peptide-bonded carrier resin obtained in Reference Example 9 was added thereto and stirred at 4° C. for 48 hours. The carrier resin was collected by filtration and washing, drying, cleavage of the peptide and purification by HPLC were carried out in the same manner as in Example 6. Thus, 21 µg of compound (8) were obtained.

Mass Analysis [FABMS]: 2035 (M+H).

Amino Acid Analysis: Asx 2.2 (3), Gly 4.1 (4), His 0. 9 (1), Arg 1.7 (2), Thr 1.1 (1), Ala 1.0 (1), Pro 1.0 (1), Ile 1.9 (2), Phe 0.8 (1), Trp (not determined).

EXAMPLE 9

Synthesis of Compound (9)

A 7.56 mg portion of compound (a) obtained in Reference Example 1 was dissolved in 1.46 ml of DMF, and 7.10 mg of PyBOP, 1.81 mg of HOBt and 2.27 gl of NMM were added thereto while cooling on ice. The resulting mixture was allowed to stand for 20 minutes still while cooling on ice. A 65 mg portion of the peptide-bonded carrier resin obtained in Reference Example 10 was added thereto and stirred at 4° C. for 24 hours. The carrier resin was collected by filtration and washing, drying, cleavage of the peptide and purification by HPLC were carried out in the same manner as in Example 6. Thus, 0.5 mg of compound (9) were obtained.

Mass Analysis [FABMS]:30 2035 (M+H).

Amino Acid Analysis: Asx 2.3 (3), Gly 4.1 (4), His 1.0 (1), Arg 1.8 (2), Thr 1.0 (1), Ala 1.0 (1), Pro 1.0 (1), Ile 2.0 (2), Phe 1.0 (1), Trp (not determined).

EXAMPLE 10

Synthesis of Compound (10)

A 7.63 mg portion of compound (a) obtained in Reference Example 1 was dissolved in 0.597 ml of DMF, and 7.08 mg of PyBOP, 2.08 mg of HOBt and 2.24 µl of NMM were added thereto while cooling on ice. The resulting mixture was allowed to stand for 20 minutes still while cooling on ice. A 38.35 mg portion of the peptide-bonded carrier resin obtained in Reference Example 11 was added thereto and stirred at 4° C. for 24 hours. The carrier resin was collected by filtration, washing, drying, cleavage of the peptide and purification by HPLC were carried out in the same manner as in Example 6. Thus, 1.8 mg of compound (10) were obtained.

Mass Analysis [FABMS]: 2049 (M+H).

Amino Acid Analysis: Asx 1.5 (3), Gly 4.0 (4), His 0.9 (1), Arg 1.8 (2), Thr 1.0 (1), Ala 1.0 (1), Pro 1.0 (1), Ile 0.9 (1), Phe 0.9 (1), (N-Me)Ile and Trp (not determined).

EXAMPLE 11

Synthesis of Compound (11)

A 6.97 mg portion of compound (a) obtained in Reference Example 1 was dissolved in 1.5 ml of DMF, and 6.55 mg of PyBOP, 1.67 mg of HOBt and 2.09 µl of NMM were added thereto while cooling on ice. The resulting mixture was allowed to stand for 5 minutes still while cooling on ice. A 38.85 mg portion of the peptide-bonded carrier resin obtained in Reference Example 12 was added thereto and stirred at 4° C. for 24 hours. The carrier resin was collected by filtration, washed with methanol and butyl ether and dried for 2 hours under reduced pressure. To the thus-obtained resin were added 600 µl of a mixed solution containing 82.5% TFA, 5% water, 5% thioanisole, 2.5% 1,2-ethanedithiol, 3% ethylmethyl sulfide and 2% thiophenol and supplemented with 5 mg/ml of 2-methylindole. The resulting mixture was allowed to stand at room temperature for 6 hours in order to remove the side-chain-protecting groups and cleave the peptide from the resin. The resin was removed by filtration, about 2 ml of ether were added to the filtrate, and the precipitate formed was collected as a crude peptide. The peptide was purified by HPLC in the same manner as in Reference Example 2 to obtain 2.0 mg of compound (11).

Mass Analysis [FABMS]: 2351 (M+H).

Amino Acid Analysis: Asx 1.2 (2), Gly 3.0 (3), His 0.8 (1), Arg 2.7 (3), Thr 1.0 (1), Ala 1.0 (1), Pro 1.6 (2), Leu 1.0 (1), Phe 1.9 (2), Ser 1.1 (1), Hyp 0.9 (1), Trp (not determined).

REFERENCE EXAMPLE 1

Synthesis of Compound (a)

Compound (a)

```
┌─────────────────────────────────────────┐
└─Gly-Asn-Trp-His-Gly-Thr-Ala-Pro-Asp-Trp-OH
```

Step 1: Fmoc-Gly-Asn-Trp-His-Gly-Thr-Ala-Pro-OH (SEQ ID NO:61)

A 0.73 g portion of a carrier resin to which 0.5 mmol. of Boc-Pro had been bonded was put into a reactor of an automatic synthesizer. According to the ABI instruction's, the following operation was carried out:

(1) treatment with a methylene chloride solution containing 33% TFA (for 80 seconds);

(2) treatment with a methylene chloride solution containing 50% TFA (for 18.5 minutes);

(3) washing with methylene chloride (three times);

(4) treatment with a methylene chloride solution containing 10% diisopropylethylamine (one minute, two times); and (5) washing with DMF (five times)

Thus, the Pro-bonded carrier resin was obtained.

Boc-Ala-Pro was produced on the carrier by:

(6) adding 4 ml of a DMF solution containing 2.0 mmol of symmetric acid anhydride of Boc-Ala-OH, followed by stirring materials in the reactor for 18 minutes; and (7) washing with methylene chloride (five times).

The carrier was then subjected to the deprotection process according to steps (1) to (5) above. After adding a symmetric anhydride of Boc-Thr(Bzl)-OH thereto, a condensation reaction was carried out according to the step (6). The resulting condensate was washed according to the above-referenced washing step (7) to produce Boc-Thr(Bzl)-Ala-Pro on the carrier resin. Thereafter, steps (1) to (7) were repeated in order, and 1.2 g of a protected peptide-bonded carrier resin were obtained. In the step (6), Boc-Gly-OH, Boc-His(Bom)-OH, Boc-Trp(CHO)-OH, Boc-Asn-OH and Fmoc-Gly-OH were used in that order. Then, 0.8 ml of 1,2-ethanedithiol, 0.8 ml of dimethyl sulfide and 0.2 ml of anisole were added to the thus-obtained carrier resin and allowed to stand for 3 hours. Eighteen ml of hydrogen fluoride were added thereto and stirred for 70 minutes while cooling on ice. Next, hydrogen fluoride was removed under reduced pressure, and 100 ml of ethyl acetate were added to the carrier resin and stirred for 0.5 hours. The carrier resin was collected by filtration, 100 ml of DMF were added thereto and the resulting mixture was stirred for 1 hour. The carrier resin was removed by centrifugation (full-automatic high-speed cooling centrifuger, RS-20 Model, Tomy Seiko KK) at 10,000 rpm for 10 minutes to obtain the supernatant. DMF was removed from the supernatant, using an evaporator, ROTARY VACUUM EVAPORATOR N-2 Model (Tokyo Rika Kiki KK), followed by treatment with 2 M acetic acid to obtain 464.0 mg of a crude product. This product was purified by HPLC, using a reversed-phase column (CAPCELL PACK C18 SG-120; 30×250 mm). Elution was carried out by linear gradient elution using an eluent system of acetonitrile/water containing 0.1% TFA. A fraction containing the intended product was obtained by detection at 220 nm. This fraction was freeze-dried to obtain 131.9 mg of Fmoc-Gly-Asn-Trp-His-Gly-Thr-Ala-Pro-OH.

Step 2: Synthesis of H-Asp(Ot-Bu)-Trp-OBzl (a) A 41 mg portion of Fmoc-Asp(Ot-Bu)-OH was dissolved in 1, ml of methylene chloride, and 12 mg of HONSu and 21 mg of DCC were added thereto at 0° C. and stirred at 0° C. for 30 minutes. Then, 1 ml of a methylene chloride solution containing 33 mg of H-Trp-OBzl hydrochloride and 14 μl of triethylamine were added thereto and stirred at 0° C. for 3 hours. The insoluble substances were removed by filtration and washed with cold methylene chloride, and the filtrate was collected. The solvent was removed from the filtrate by distillation under reduced pressure, and the residue was purified by silica gel column chromatography (50 g of Wakogel C-200, eluted with chloroform/methanol=25/1) to obtain 67 mg of Fmoc-Asp(Ot-Bu)-Trp-OBzl as a white powder.

(b) Ten mg of the dipeptide obtained in the above-referenced (a) were dissolved in 3 ml of DMF, and 0.75 ml of piperidine were added thereto and allowed to stand at room temperature for 10 minutes. Ether and hexane were added to the reaction mixtures and the white precipitate was collected by filtration. This was dried under reduced pressure to obtain 2 mg of H-Asp(Ot-Bu)-Trp-OBzl.

Step 3: Synthesis of H-Gly-Asn-Trp-His-Gly-Thr-Ala-Pro-Asp-Trp-OBzl (SEQ ID NO:62)

(a) To 4.4 mg of the peptide obtained in the above-referenced step 1 were added 5.5 ml of a DMF solution containing 1.7 mg of the dipeptide obtained in the above-referenced step 2. After cooling to 0° C., 0.5 μl of DEPC and 1.0 μl of triethylamine were added in that order and stirred at 0° C. for 5 days. The solvent was removed by distillation under reduced pressure, and the residue was dissolved in 1 ml of DMF and purified by HPLC using a reversed-phase column (YMC-Pack ODS-AM; 150×6 mm I.D.) to obtain 320 μg of Fmoc-Gly-Asn-Trp-His-Gly-Thr-Ala-Pro-Asp(Ot-Bu)-Trp-OBzl (SEQ ID NO:63) as a white powder.

(b) A 50 μl portion of a mixture containing 900 μl of TFA, 50 μl of 1,2-ethanedithiol, 50 μl of anisole and 5 mg of 2-methylindole were added to 250 μg of the protected peptide obtained in the above-mentioned (a) and allowed to stand at room temperature for 1.5 hours. Ether was added thereto, and the white precipitate-that formed was collected by filtration and dried. After adding 100 μl of DMF containing 20% piperidine, the mixture was allowed to stand at room temperature for 15 minutes. Ether was again added thereto, and the white precipitate that formed was collected by filtration and dried. Thus, 200 μg of H-Gly-Asn-Trp-His-Gly-Thr-Ala-Pro-Asp-Trp-OBzl were obtained.

Step 4: Synthesis of Compound (a)

(a) In 60 μl of DMF were dissolved 66 μg of the peptide obtained in the above-mentioned step 3. Then, 1.6 μl of a DMF solution containing 0.1 M PyBOP, 1.6 μl of a DMF solution containing 0.1 M HOBt and 3 μl of a DMF solution containing 1% NMM were added thereto at room temperature and stirred for 3 hours still at room temperature. The solvent was removed by distillation under reduced pressure, and the product was purified by HPLC in the same manner as in the above-mentioned step 3 to obtain 20 μg of benzyl ester of compound (a).

(b) A 250 μg portion of the benzyl ester obtained in the above-mentioned (a) was dissolved in 80 μl of a mixture of methanol/acetic acid=3/1, about 0.5 mg of 10% Pd/C were added thereto in nitrogen atmosphere. After the atmosphere was substituted with hydrogen atmosphere, the mixture was stirred at room temperature for 1 hour. The Pd/C was removed by filtration, ether was added to the filtrate, and the white precipitate formed was collected by filtration and dried to obtain 100 μg of compound (a).

Mass Analysis [FABMS]: 1122 (M+H).

Amino Acid Analysis: Gly 2.0 (2), Asx 1.7 (2), His 1.0 (1), Thr 1.0 (1), Ala 1.0 (1), Pro 1.0 (1), Trp (not determined).

REFERENCE EXAMPLE 2

Synthesis of Compound (b)
(H-Val-Thr-Gly-Arg-Gly-Asp-Ser-Pro-Ala-OH: SEQ ID NO:64)

Fifty mg of a carrier resin (Fmoc-Ala-Wang Resin), to which 30 μmol of Fmoc-Ala had been bonded, were put into a reactor of an automatic synthesizer and the following operation was carried out according to the instructions provided by Shimadzu Corporation.

(a) The carrier resin was washed with DMF for 3 minutes, and the solution was discharged.

(b) A DMF solution containing 30% piperidine was added thereto and stirred for 4 minutes, and the solution was discharged. This operation was repeated once more.

(c) The carrier resin was washed with DMF for one minute, and the solution was discharged. This operation was repeated five times.

Thus, an Ala-bonded carrier resin from which the Fmoc group had been removed was obtained.

(d) In 840 μl of DMF, 240 μmol of Fmoc-Pro-OH, 240 μmol of PyBOP, 240 μmol of HOBt and 360 μmol of NMM were stirred for 3 minutes, and the resulting solution was added to the resin and stirred for 30 minutes. The solution was discharged.

(e) The carrier resin was washed with DMF for one minute, and this operation was repeated five times. Thus, Fmoc-Pro-Ala was produced on the carrier.

Next, after the washing and deprotection steps according to the above-referenced (a) to (c), a condensation reaction was carried out using Fmoc-Ser(t-Bu)-OH according to the above-referenced step (d), followed by the washing step according to the above-referenced step (e). Thus, Fmoc-Ser(t-Bu)-Pro-Ala was produced on the carrier. Thereafter, the above-referenced steps (a) to (e) were repeated, using Fmoc-Asp(Ot-Bu)-OH, Fmoc-Gly-OH, Fmoc-Arg(Pmc)-OH, Fmoc-Gly-OH, Fmoc-Thr(t-Bu)-OH and Fmoc-Val-OH in this order in the step (d) to obtain a protected peptide-bonded carrier resin. The resulting carrier was again washed and deprotected according to the above-referenced steps (a) to (c), and washed with methanol and butyl ether and dried for 3 hours under reduced pressure. A 50 mg portion of the carrier resin thus obtained were separated. To the remaining carrier resin added were 200 μl of a mixed solution containing 82.5% TFA, 5% thioanisole, 5% water, 3% ethylmethyl sulfide, 2.5% 1,2-ethanedithiol and 2% thiophenol. The resulting mixture was then allowed to stand at room temperature for 8 hours in order to remove the side-chain-protecting groups and cleave the peptide from the resin. Then, the resin was removed by filtration, about 10 ml of ether were added to the filtrate, and the precipitate formed was collected. Thus, 17.9 mg of a crude peptide were obtained. This crude product was purified by HPLC using a reversed-phase column (CAPCELL PAK C18; 30 mmø×250 mm; Shiseido Co., Ltd.). Elution was carried out by linear gradient elution using acetonitrile (0–90%) containing 0.1% of TFA, and detection was made at 220 nm to obtain a fraction containing the desired compound. This fraction was freeze-dried to obtain 6.2 mg of compound (b).

Mass Analysis [FABMS]: 859 (M+H).

Amino Acid Analysis: Gly 2.1 (2), Ala 1.0 (1), Asx 1.0 (1), Pro 0.9 (1), Thr 0.9 (1), Val 0.9 (1), Ser 1.0 (1), Arg 1.0 (1).

REFERENCE EXAMPLE 3

Synthesis of Compound (c)
(H-Val-Tyr-Ala-Val-Thr-Gly-Arg-Gly-Asp-Ser-Pro-Ala-NH$_2$: SEQ ID NO:65)

A protected peptide was produced in the same manner as in Reference Example 2, using, as the starting material, a carrier resin (Rink Amide MBHA Resin) to which 40.8 μmol of Fmoc-NH had been bonded and using, as N-protected amino acids, Fmoc-Ala-OH, Fmoc-Pro-OH, Fmoc-Ser(t-Bu)-OH, Fmoc-Asp(Ot-Bu)-OH, Fmoc-Gly-OH, Fmoc-Arg(Pmc)-OH, Fmoc-Gly-OH, Fmoc-Thr(t-Bu)-OH, Fmoc-Val-OH, Fmoc-Ala-OH, Fmoc-Tyr(t-Bu)-OH, Fmoc-Val-OH in this order. The peptide was cleaved from 50 mg of the thus-obtained carrier resin and purified by HPLC, in the same manner as in Reference Example 2. Thus, 12.6 mg of compound (c) were obtained.

Mass Analysis [FABMS]: 1191 (M+H).

Amino Acid Analysis: Asx 0.9 (1), Gly 1.7 (2), Thr 1.0 (1), Ala 2.0 (2), Pro 0.9 (1), Val 1.9 (2), Tyr 0.9 (1), Arg 1.0 (1), Ser 0.9 (1).

REFERENCE EXAMPLE 4

Synthesis of Compound (d)
(H-Ser-Met-Gly-Leu-Pro-Cys-Val-Val-Met-OH: SEQ ID NO:66)

Eighty mg of a carrier resin (Fmoc-Met-Wang Resin), to which 38 μmol of Fmoc-Met had been bonded, were put into a reactor of an automatic synthesizer and the following operation was carried out according to the instructions provided by Shimadzu Corporation.

(a) The carrier resin was washed with DMF for 3 minutes, and the solution was discharged.

(b) A DMF solution containing 30% piperidine was added thereto and stirred for 4 minutes, and the solution was discharged. This operation was repeated once more.

(c) The carrier resin was washed with DMF for one minute, and the solution was discharged. This operation was repeated five times.

Thus, a Met-bonded carrier resin from which the Fmoc group had been removed was obtained.

(d) In 665 μl of DMF, 190 μmol of Fmoc-Val-OH, 190 μmol of PyBOP, 190 μmol of HOBt and 285 μmol of NMM were stirred for 3 minutes, and the resulting solution was added to the resin and stirred for 30 minutes. The solution was discharged.

(e) The, carrier resin was washed with DMF for one minute, and this operation was repeated five times. Thus, Fmoc-Val-Met was synthesized on the carrier.

Next, the resulting resin was washed and deprotected according to the above-referenced steps (a) to (c) and a condensation reaction was carried out using Fmoc-Val-OH according to the above-referenced step (d). After the washing step according to the above-referenced step (e), Fmoc-Val-Val-Met was synthesized on the carrier. Thereafter, the above-referenced steps (a) to (e) were repeated, using Fmoc-Cys(Trt)-OH, Fmoc-Pro-OH, Fmoc-Leu-OH, Fmoc-Gly-OH, Fmoc-Met-OH and Fmoc-Ser(t-Bu)-OH in that order in the step (d). Thus, a protected peptide-bonded carrier resin was produced. The resulting carrier was again washed and deprotected according to the above-referenced steps (a) to (c), washed with methanol and butyl ether, and dried for 3 hours under reduced pressure to obtain 120.9 mg of a protected peptide-bonded carrier resin. To a 40.3 mg portion of the resin were added 400 μl of a mixed solution containing 90% TFA, 5% 1,2-ethanedithiol and 5% thioanisole. The resulting mixture was then allowed to stand at room temperature for 2 hours in order to remove the side-chain-protecting groups and cleave the peptide from the resin. Then, the resin was removed by filtration, about 10 ml of ether were added to the filtrate, and the precipitate formed was collected by centrifugation to obtain 12.7 mg of a crude peptide. This crude product was purified by HPLC in the same manner as in Reference Example 2 to obtain 6.2 mg of compound (d).

Mass Analysis [FABMS]: 936 (M+H).

Amino Acid Analysis: Gly 1.1 (1), Pro 0.9 (1), Val 1.2 (2), Ser 0.9 (1), Met 1.9 (2), Leu 1.0 (1), Cys (not determined).

REFERENCE EXAMPLE 5

Synthesis of Compound (e)
(H-Ser-Ser-Gly-Cys-Val-Leu-Ser-OH: SEQ ID NO:67)

In the same manner as in Reference Example 4, 99.3 mg of a protected peptide-bonded carrier resin were obtained using, as the starting material, 70 mg of a carrier resin (Fmoc-Ser(t-Bu)-Wang Resin) to which 59.0 $\mu$mol of Fmoc-Ser(t-Bu) had been bonded and using, as N-protected amino acids, Fmoc-Leu-OH, Fmoc-Val-OH, Fmoc-Cys(Trt)-OH, Fmoc-Gly-OH, Fmoc-Ser(t-Bu)-OH and Fmoc-Ser(t-Bu)-OH in that order. The peptide was cleaved from 33.1 mg of the thus-obtained carrier resin and purified by HPLC, in the same manner as in Reference Example 4. Thus, 5.3 mg of compound (e) were obtained.

Mass Analysis [FARMS]: 652 (M+H).

Amino Acid Analysis: Gly 1.1 (1), Val 0.8 (1), Ser 2.9 (3), Leu 1.0 (1), Cys (not determined).

REFERENCE EXAMPLE 6

Synthesis of Compound (f)
(H-Ser-Met-Gly-Leu-Pro-Cys-Ile-Phe-Met-OH: SEQ ID NO:68)

In the same manner as in Reference Example 4, 120.8 mg of a protected peptide-bonded carrier resin were obtained using, as the starting material, 80 mg of a carrier resin (Fmoc-Met-Wang Resin) to which 52.0 $\mu$mol of Fmoc-Met had been bonded and using, as N-protected amino acids, Fmoc-Phe-OH, Fmoc-Ile-OH, Fmoc-Cys(Trt)-OH, Fmoc-Pro-OH, Fmoc-Leu-OH, Fmoc-Gly-OH, Fmoc-Met-OH and Fmoc-Ser(t-Bu)-OH in that order. To 40.3 mg of the carrier resin thus obtained were added 600 $\mu$l of a mixed solution containing 90% TFA, 5% thioanisole and 5% 1,2-ethanedithiol and supplemented with 5 mg/ml of 2-methylindole. The resulting mixture was allowed to stand at room temperature for 2 hours in order to remove the side-chain-protecting groups and cleave the peptide from the resin. Then, the resin was removed by filtration, and about 2 ml of ether were added to the filtrate. The precipitate thus formed was obtained as a crude peptide. The peptide was purified by HPLC also in the same manner as in Reference Example 4 to obtain 8.8 mg of compound (f).

Mass Analysis [FABMS]: 998 (M+H).

Amino Acid Analysis Ser 1.0 (1), Gly 1.1 (1), Pro 1.1 (1), Met 1.9 (2), Ile 0.9 (1), Leu 1.0 (1), Phe 0.9 (1), Cys (not determined).

REFERENCE EXAMPLE 7

Synthesis of Compound (g)
(H-Phe-Gly-Gly-Arg-Ile-Asp-Arg-Ile-NH$_2$: SEQ ID NO:69)

Eighty mg of a carrier resin (Rink amide MBHA Resin), to which 40.8 $\mu$mol of Fmoc-NH had been bonded, were put into a reactor of an automatic synthesizer and the following operation was carried out according to the instructions provided by Shimadzu Corporation.

(a) The carrier resin was washed with DMF for 3 minutes, and the solution was discharged.

(b) A DMF solution containing 30% piperidine was added. there to and stirred for 4 minutes, and the solution was discharged. This operation was repeated once more.

(c) The carrier resin was washed with DMF for one minute, and the solution was discharged. This operation was repeated five times.

Thus, an NH-bonded carrier resin from which the Fmoc group had been removed was obtained.

(d) In 714 $\mu$l of DMF, 2040 $\mu$mol of Fmoc-Ile-OH, 204 $\mu$mol of PyBOP, 204 $\mu$mol of HOBt and 306 $\mu$mol of NMM were stirred for 3 minutes, and the resulting solution was added to the resin and stirred for 30 minutes. The solution was discharged.

(e) The carrier resin was washed with DMF for one minute, and this operation was repeated five times. Then, Fmoc-Ile was synthesized on the carrier.

Next, the resulting carrier was washed and deprotected according to the above-referenced steps (a) to (c) and a condensation reaction was carried out using Fmoc-Arg(Pmc)-OH according to the above-referenced step (d). After the washing step according to the above-referenced step (e), Fmoc-Arg(Pmc)-Ile was synthesized on the carrier. Next, the above-referenced steps (a) to (e) were repeated, using Fmoc-Asp(Ot-Bu)-OH, Fmoc-Ile-OH, Fmoc-Arg(Pmc)-OH, Fmoc-Gly-OH, Fmoc-Gly-OH and Fmoc-Phe-OH in that order in the step (d). Thus, a protected peptide-bonded carrier resin was produced. The resulting resin was again washed and deprotected according to the above-referenced steps (a) to (c), washed with methanol and butyl ether, and dried for 3 hours under reduced pressure to obtain 122.1 mg of a protected peptide-bonded carrier resin. To 40.7 mg of the resin added were 600 $\mu$l of a mixed solution containing 82.5% TFA, 5% thioanisole, 5% water, 3% ethylmethyl sulfide, 2.5% 1,2-ethanedithiol and 2% thiophenol. The resulting mixture was then allowed to stand at room temperature for 8 hours in order to remove the side-chain-protecting groups and cleave the peptide from the resin. Then, the resin was removed by filtration, about 2 ml of ether were added to the filtrate, and the precipitate formed was collected to obtain 16.2 mg of a crude peptide. This crude product was purified by HPLC in the same manner as in Reference Example 2 to obtain 12.0 mg of compound (g).

Mass Analysis [FABMS]: 932 (M+H).

Amino Acid Analysis: Asx 1.0 (1), Gly 2.1 (2), Arg 1.9 (2), Ile 2.0 (2), Phe 1.0 (1).

REFERENCE EXAMPLE 8

Synthesis of Compound (h)
(H-Ala-Phe-Gly-Gly-Arg-Ile-Asp-Arg-Ile-Gly-Ala-Ala-NH$_2$: SEQ ID NO:70 )

In the same manner as in Reference Example 7, 147.1 mg of a protected peptide-bonded carrier resin were obtained using, as the starting material, 80 mg of a carrier resin (Rink amide MBHA Resin) to which 40.8 $\mu$mol of Fmoc-NH had been bonded and using, as N-protected amino acids, Fmoc-Ala-OH, Fmoc-Ala-OH, Fmoc-Gly-OH, Fmoc-Ile-OH, Fmoc-Arg(Pmc)-OH, Fmoc-Asp(Ot-Bu)-OH, Fmoc-Ile-OH, Fmoc-Arg(Pmc)-OH, Fmoc-Gly-OH, Fmoc-Gly-OH, Fmoc-Phe-OH and Fmoc-Ala-OH in that order. The peptide was cleaved from 49.0 mg of the thus-obtained carrier resin and purified by HPLC, also in the same manner as in Reference Example 7. Thus, 13.6 mg of compound (h) were obtained.

Mass Analysis [FABMS]: 1202 (M+H).
Amino Acid Analysis: Asx 0.9 (1), Gly 3.0 (3), Arg 1.8 (2), Ala 3.0 (3), Ile 1.9 (2), Phe 0.9 (1).

REFERENCE EXAMPLE 9

Synthesis of Compound (i)
(H-Phe-Gly-Gly-D-Arg-Ile-Asp-Arg-Ile-NH$_2$ (SEQ ID NO:71)):

In the same manner as in Reference Example 7, 221.5 mg of a protected peptide-bonded carrier resin were obtained using, as the starting material, 80 mg of a carrier resin (Rink amide MBHA Resin) to which 40.8 μmol of Fmoc-NH had been bonded and using, as N-protected amino acids, Fmoc-Ile-OH, Fmoc-Arg(Pmc)-OH, Fmoc-Asp(Ot-Bu)-OH, Fmoc-Ile-OH, Fmoc-D-Arg(Pmc)-OH, Fmoc-Gly-OH, Fmoc-Gly-OH and Fmoc-Phe-OH in that order. The peptide was cleaved from 72.2 mg of the thus-obtained carrier resin and purified by HPLC, also in the same manner as in Reference Example 7. Thus, 13.8 mg of compound (i) were obtained.

Mass Analysis [FABMS]: 932 (M+H).
Amino Acid Analysis: Asx 1.0 (1), Gly 2.1 (2), Arg 1.8 (2), Ile 1.9 (2), Phe 1.0 (1).

REFERENCE EXAMPLE 10

Synthesis of Compound (j)
(H-Phe-Gly-Gly-D-Arg-Ile-Asp-D-Arg-Ile-NH$_2$)

In the same manner as in Reference Example 7, 202.0 mg of a protected peptide-bonded carrier resin were obtained using, as the starting material, 80 mg of a carrier resin (Rink amide MBHA Resin) to which 40.8 μmol of Fmoc-NH had been bonded and using, as N-protected amino acids, Fmoc-Ile-OH, Fmoc-D-Arg(Pmc)-OH, Fmoc-Asp(Ot-Bu)-OH, Fmoc-Ile-OH, Fmoc-D-Arg(Pmc)-OH, Fmoc-Gly-OH, Fmoc-Gly-OH and Fmoc-Phe-OH in that order. The peptide was cleaved from 72.0 mg of the thus-obtained carrier resin and purified by HPLC, also in the same manner as in Reference Example 7. Thus, 11.3 mg of compound (j) were obtained.

Mass Analysis [FABMS]: 932 (M+H).
Amino Acid Analysis: Asx 1.0 (1), Gly 2.1 (2), Arg 1.8 (2), Ile 1.9 (2), Phe 1.0 (1).

REFERENCE EXAMPLE 11

Synthesis of Compound (k)
(H-Phe-Gly-Gly-Arg-(N-Me)Ile-Asp-Arg-Ile-NH$_2$: SEQ ID NO:11)

A resin to which (N-Me)Ile-Asp-Arg-Ile had been bonded was obtained in the same manner as in Reference Example 7, using, as the starting material, 80 mg of a carrier resin (Rink amide MBHA Resin) to which 40.8 μmol of Fmoc-NH had been bonded and using, as N-protected amino acids, Fmoc-Ile-OH, Fmoc-Arg(Pmc)-OH, Fmoc-Asp(Ot-Bu)-OH, and Fmoc-(N-Me)Ile-OH in that order. One ml of a DMF solution containing 135.2 mg of Fmoc-Arg(Pmc)-OH and 104.6 mg of PyBroP were added thereto and 71 μl of DIEA were further added thereto while cooling on ice. The resulting mixture was allowed to stand for 10 minutes still while cooling on ice, and thereafter stirred at room temperature for 21 hours. The resin was collected by filtration and washed five times each with 1 ml of DMF to obtain a resin to which Fmoc-Arg(Pmc)-(N-Me)Ile-Asp(Ot-Bu)-Arg (Pmc)-Ile had been bonded. Then, the resulting resin was condensed with, as a Fmoc-amino acids, Fmoc-Gly-OH, Fmoc-Gly-OH and Fmoc-Phe-OH in that order, according to the same synthesis program as in Reference Example 7, and 115.0 mg of a protected peptide-bonded carrier resin were obtained. The peptide was cleaved from 38.3 mg of the thus-obtained carrier resin and purified by HPLC, also in the same manner as in Reference Example 7. Thus, 1.3 mg of compound (k) were obtained.

Mass Analysis [FABMS]: 946 (M+H).
Amino Acid Analysis: Asx 0.9 (1), Gly 2.1 (2), Arg 2.0 (2), Ile 1.0 (1), Phe 1.0 (1), (N-Me)Ile (not determined).

REFERENCE EXAMPLE 12

Synthesis of Compound (m)
(H-D-Arg-Arg-Pro-Hyp-Gly-Phe-Ser-D-Phe-Leu-Arg-OH)

In the same manner as in Reference Example 7, 116.5 mg of a protected peptide-bonded carrier resin were obtained using, as the starting material, 80 mg of a carrier resin (Fmoc-Arg(Pmc)-Wang Resin) to which 37.6 μmol of Fmoc-Arg(Pmc) had been bonded and using, as N-protected amino acids, Fmoc-Leu-OH, Fmoc-D-Phe-OH, Fmoc-Ser(t-Bu)-OH, Fmoc-Phe-OH, Fmoc-Gly-OH, Fmoc-Hyp(t-Bu)-OH, Fmoc-Pro-OH, Fmoc-Arg(Pmc)-OH and Fmoc-D-Arg (Pmc)-OH in that order. The peptide was cleaved from 38.8 mg of the thus-obtained carrier resin and purified by HPLC, also in the same manner as in Reference Example 7. Thus, 6.3 mg of compound (m) were obtained.

Mass Analysis [FABMS]: 1248 (M+H).
Amino Acid Analysis: Hyp 1.1 (1), Ser 1.1 (1), Gly 1.2 (1), Arg 3.1 (3), Pro 0.9 (1), Leu 1.0 (1), Phe 2.0 (2).

INDUSTRIAL APPLICABILITY

The present invention provides novel peptides in which a cyclic peptide having a specific structure is bonded to a physiologically active peptide optionally via a spacer. The peptides of the present invention have higher stability and/or higher activity than physiologically active peptides to which no cyclic peptide is bonded.

What is claimed is:

1. A peptide represented by the following formula (A):

$$M-X^1-X^2-X^3-X^4-X^5-X^6-Pro-Asp-(Trp)n-Q \quad (A)$$

wherein $X^1$ represents an α-amino acid residue selected form the group consisting of Asn, Gln and His;

$X^2$ represents an α-amino acid residue selected form the group consisting of Trp, Tyr and Phe;

$X^3$ represents an α-amino acid residue selected form the group consisting of His, Asn and Gln;

$X^4$ represents an α-amino acid residue selected form the group consisting of Gly and Ala;

$X^5$ represents an α-amino acid residue selected form the group consisting of Thr and Ser;

$X^6$ represents an α-amino acid residue selected form the group consisting of Ala, Gly and Ser;

M represents Gly or Cys; and n represents an integer of from 0 to 3, and Q is represented by a formula selected from the group consisting of formula (I), (II), (III) and (IV), wherein formula (I) is

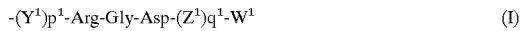

wherein $Y^1$ and $Z^1$ each represent an α-amino acid residue; $W^1$ represents a hydroxy, lower alkoxy or amino group; $p^1$ represents an integer of from 0 to 8; $q^1$ represents an integer of from 0 to 10; and the α-amino acid residues to be represented by $Y^1$'s when $p^1$ is 2 or more or by $Z^1$'s when $q^1$ is 2 or more are the same or different;

formula (II) is

wherein $A^2$, $B^2$ and $C^2$ each represent an α-amino acid residue; p2 represents an integer of from 0 to 8; $Y^2$ represents an α-amino residue; $W^2$ represents a hydroxy, lower alkoxy or amino group; and the α-amino acid residues to be represented by $Y^2$'s when $p^2$ is 2 or more are the same or different;

formula (III) is

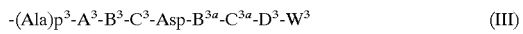

wherein $p^3$ represents an integer of from 0 to 1; $W^3$ represents a hydroxy, lower alkoxy or amino group; $A^3$ represents Phe, Gly, Phe-Gly, Gly-Gly, Phe-Gly-Gly or a single bond; $B^3$ and $B^{3a}$ are the same or different and each represents Arg or D-Arg; $C^3$ and $C^{3a}$ are the same or different and each represents Ile or (N-methyl)Ile; $D^3$ represents Gly, Ala, Gly-Ala, Ala-Ala, Gly-Ala-Ala or a single bond; and formula (IV) is

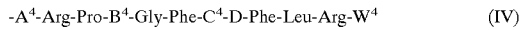

wherein $A^4$ represents Arg, D-Arg, or a single bond; $B^4$ represents a hydroxyproline or Pro; $C^4$ represents Ser or Cys; $W^4$ represents a hydroxy, lower alkoxy or amino group, or a pharmaceutically acceptable salt thereof.

2. The peptide as claimed in claim 1, wherein Q is represented by the following formula (I)

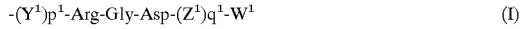

wherein $Y^1$ and $Z^1$ each represent an α-amino acid residue; $W^1$ represents a hydroxy, lower alkoxy or amino group; $p^1$ represents an integer of from 0 to 8; $q^1$ represents an integer of from 0 to 10; and the α-amino acid residues to be represented by $Y^1$'s when $p^1$ is 2 or more or by $Z^1$'s when $q^1$ is 2 or more are the same or different.

3. The peptide as claimed in claim 1, wherein Q is represented by the following formula (II):

wherein $A^2$, $B^2$ and $C^2$ each represent an α-amino acid residue; $p^2$ represents an integer of from 0 to 8; $Y^2$ represents an α-amino acid residue; $W^2$ represents a hydroxy, lower alkoxy or amino group; and the α-amino acid residues to be represented by $Y^2$'s when p is 2 or more are the same or different.

4. The peptide as claimed in claim 1, wherein Q is represented by the following formula (III):

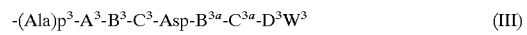

wherein $p^3$ represents an integer of from 0 to 1; $W^3$ represents a hydroxy, lower alkoxy or amino group; $A^3$ represents Phe, Gly, Phe-Gly, Gly-Gly, Phe-Gly-Gly or a single bond; $B^{3a}$ and $B^{3a}$ are the same or different and each represents Arg or D-Arg; $C^3$ and $C^{3a}$ are the same or different and each represents Ile or (N-methyl)Ile; $D^3$ represents Gly, Ala, Gly-Ala, Ala-Ala, Gly-Ala-Ala or a single bond.

5. The peptide as claimed in claim 1, wherein Q is represented by the following formula (IV):

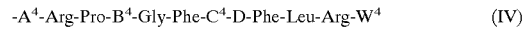

wherein $A^4$ represents Arg; D-Arg or a single bond; $B^4$ represents a hydroxy proline or Pro; $C^4$ represents Ser or Cys; $W^4$ represents a hydroxy, lower alkoxy or amino group.

6. The peptide of claim 1 wherein $X^1$-$X^2$-$X^3$-$X^4$-$X^5$-$X^6$-Pro is NWHGTAP.

7. The peptide of claim 2 wherein $X^1$-$X^2$-$X^3$-$X^4$-$X^5$-$X^6$-Pro is NWHGTAP.

8. The peptide of claim 3 wherein $X^1$-$X^2$-$X^3$-$X^4$-$X^5$-$X^6$-Pro is NWHGTAP.

9. The peptide of claim 4 wherein $X^1$-$X^2$-$X^3$-$X^4$-$X^5$-$X^6$-Pro is NWHGTAP.

10. The peptide of claim 5 wherein $X^1$-$X^2$-$X^3$-$X^4$-$X^5$-$X^6$-Pro is NWHGTAP.

* * * * *

SEQUENCE LISTING (1) GENERAL INFORMATION:

(iii) NUMBER OF SEQUENCES: 72

(2) INFORMATION FOR SEQ ID NO: 1:

(i) SEQUENCE CHARACTERISTICS:
       (A) LENGTH: 9 amino acids

```
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 1:

Val Thr Gly Arg Arg Gly Asp Ser Pro
1               5

(2) INFORMATION FOR SEQ ID NO: 2:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 2:

Val Tyr Ala Val Thr Gly Arg Gly Asp Ser Pro Ala
1               5                   10

(2) INFORMATION FOR SEQ ID NO: 3:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 3:

Gly Arg Gly Asp Ser
1               5

(2) INFORMATION FOR SEQ ID NO: 4:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 15
            (D) OTHER INFORMATION: /note= "Xaa OH or amino acid
                residue"

(ix) FEATURE:
            (A) NAME/KEY: Modified-site
            (B) LOCATION: 1
            (D) OTHER INFORMATION: /note= "Xaa = H or amino acid"

(xi) SEQUENCE DESCRIPTION: SEQ ID NO: 4:

Xaa Cys Xaa Xaa Xaa Arg Gly Asp Xaa Xaa Xaa Xaa Xaa Cys Xaa
1               5                   10                  15

(2) INFORMATION FOR SEQ ID NO: 5:

(i) SEQUENCE CHARACTERISTICS:
            (A) LENGTH: 9 amino acids
            (B) TYPE: amino acid
            (C) STRANDEDNESS: single
            (D) TOPOLOGY: linear
```

```
        (ii) MOLECULE TYPE: peptide (xi) SEQUENCE DESCRIPTION: SEQ ID NO: 5:

Cys Met Gly Leu Pro Cys Val Val Met
1               5

(2) INFORMATION FOR SEQ ID NO: 6:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 6:

Ser Ser Gly Cys Val Leu Ser
1               5

(2) INFORMATION FOR SEQ ID NO: 7:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 7:

Phe Gly Gly Arg Ile Asp Arg Ile
1               5

(2) INFORMATION FOR SEQ ID NO: 8:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 8:

Ala Phe Gly Gly Arg Ile Asp Arg Ile Gly Ala Ala
1               5                   10

(2) INFORMATION FOR SEQ ID NO: 9:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa=Arg,D-Arg or single
                bond"

(ix) FEATURE:
            (A) NAME/KEY: Modified-site
            (B) LOCATION: 4
            (D) OTHER INFORMATION: /note= "Xaa=hydroxyproline or
                Proline"

(ix) FEATURE:
```

(A) NAME/KEY: Modified-site
            (B) LOCATION: 7
            (D) OTHER INFORMATION: /note= "Xaa=Ser or Cys"

(ix) FEATURE:
            (A) NAME/KEY: Modified-site
            (B) LOCATION: 11
            (D) OTHER INFORMATION: /note= "Xaa = hydroxy, lower alkoxy
                or amino group"

(xi) SEQUENCE DESCRIPTION: SEQ ID NO: 9:

Xaa Arg Pro Xaa Gly Phe Xaa Xaa Leu Arg Xaa
1               5                   10

(2) INFORMATION FOR SEQ ID NO: 10:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 10:

Ser Ala Ala Val Tyr Phe
1               5

(2) INFORMATION FOR SEQ ID NO: 11:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 11:

Phe Ile Gly Trp Gly Asn
1               5

(2) INFORMATION FOR SEQ ID NO: 12:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 12:

Tyr Pro Trp Trp Asn Tyr Arg
1               5

(2) INFORMATION FOR SEQ ID NO: 13:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 13:

Leu Gly Val Gly Ser Xaa Asn
1               5

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Ile Cys Lys Arg Ala
1               5

(2) INFORMATION FOR SEQ ID NO: 15:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Ile Ser Lys Arg Ala
1               5

(2) INFORMATION FOR SEQ ID NO: 16:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

Ile Ala Lys Arg Ala
1               5

(2) INFORMATION FOR SEQ ID NO: 17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

Tyr Ile Gly Ser Arg
1               5

(2) INFORMATION FOR SEQ ID NO: 18:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

Tyr Ala Val Thr Gly
1               5

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Val Tyr Ala Val Thr Gly
1               5

(2) INFORMATION FOR SEQ ID NO: 20:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Lys Gly Thr Ile Cys Arg Arg Ala
1               5

(2) INFORMATION FOR SEQ ID NO: 21:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Ser Pro Cys Ala
1

(2) INFORMATION FOR SEQ ID NO: 22:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ser Pro Ser Ala
1

(2) INFORMATION FOR SEQ ID NO: 23:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

Gly Phe Gly Ser

-continued (2) INFORMATION FOR SEQ ID NO: 24:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 24:

Asp Leu Asp Asp Tyr
1               5

(2) INFORMATION FOR SEQ ID NO: 25:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Asp Asp Met Asp Asp Tyr
1               5

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Asp Asp Gly Asp Asp Tyr
1               5

(2) INFORMATION FOR SEQ ID NO: 27:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Asp Asp Ser Asp Asp Tyr
1               5

(2) INFORMATION FOR SEQ ID NO: 28:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

```
Ser Pro Ala Ser Ser Lys
1               5
```

(2) INFORMATION FOR SEQ ID NO: 29:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

```
Asp Leu Asp Asp Tyr Cys Asn
1               5
```

(2) INFORMATION FOR SEQ ID NO: 30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

```
Asp Leu Asp Asp Tyr Ser Asn
1               5
```

(2) INFORMATION FOR SEQ ID NO: 31:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

```
Ser Met Gly Leu Pro
1               5
```

(2) INFORMATION FOR SEQ ID NO: 32:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

```
Gly Ser Met Ser Cys Lys
1               5
```

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

```
Gly Ala Met Ser Cys Lys
1               5

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

Cys Val Lys Ile Lys Lys
1               5

(2) INFORMATION FOR SEQ ID NO: 35:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

Lys Lys Ser Lys Thr Lys
1               5

(2) INFORMATION FOR SEQ ID NO: 36:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

Lys Lys Ser Arg Thr Arg
1               5

(2) INFORMATION FOR SEQ ID NO: 37:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Gly Cys Met Gly Leu Pro
1               5

(2) INFORMATION FOR SEQ ID NO: 38:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide
```

```
        (xi) SEQUENCE DESCRIPTION: SEQ ID NO: 38:

Gly Cys Met Gly Ser Pro
1               5

(2) INFORMATION FOR SEQ ID NO: 39:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 39:

Gly Lys Lys Lys Ser Gly
1               5

(2) INFORMATION FOR SEQ ID NO: 40:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 40:

Asn Gly Cys Ile Asn Cys
1               5

(2) INFORMATION FOR SEQ ID NO: 41:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 41:

Asn Lys Arg Arg Arg Gly
1               5

(2) INFORMATION FOR SEQ ID NO: 42:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 42:

Lys Pro Lys Lys Lys Ser
1               5

(2) INFORMATION FOR SEQ ID NO: 43:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide
```

(xi) SEQUENCE DESCRIPTION: SEQ ID NO: 43:

Ala Arg Lys Lys Ser Ser
1               5

(2) INFORMATION FOR SEQ ID NO: 44:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 44:

Asp Pro Cys Cys Ser Ala
1               5

(2) INFORMATION FOR SEQ ID NO: 45:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 45:

Lys Lys Arg Lys Arg Lys
1               5

(2) INFORMATION FOR SEQ ID NO: 46:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 46:

Arg Gln Gln Lys Arg Ala
1               5

(2) INFORMATION FOR SEQ ID NO: 47:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 47:

Lys Arg Ile Arg Glu Arg
1               5

(2) INFORMATION FOR SEQ ID NO: 48:

(i) SEQUENCE CHARACTERISTICS:
         (A) LENGTH: 6 amino acids
         (B) TYPE: amino acid
         (C) STRANDEDNESS: single
         (D) TOPOLOGY: linear

```
    (ii) MOLECULE TYPE: peptide (xi) SEQUENCE DESCRIPTION: SEQ ID NO: 48:

Lys Ser Phe Lys Glu Arg
1               5

(2) INFORMATION FOR SEQ ID NO: 49:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Gln Pro Thr Arg Asn Gln
1               5

(2) INFORMATION FOR SEQ ID NO: 50:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Thr Gln Ser Pro Gln Asn
1               5

(2) INFORMATION FOR SEQ ID NO: 51:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Ala Pro Ala Pro Gln Cys
1               5

(2) INFORMATION FOR SEQ ID NO: 52:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Gln Val Ala Pro Gln Asn
1               5

(2) INFORMATION FOR SEQ ID NO: 53:

(i) SEQUENCE CHARACTERISTICS:
        (A) LENGTH: 6 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO: 53:

Lys Ser Gly Asn Lys Asn
1               5

(2) INFORMATION FOR SEQ ID NO: 54:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 54:

Arg Ala Trp Asn Lys Ser
1               5

(2) INFORMATION FOR SEQ ID NO: 55:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 55:

Arg Lys Pro Glu Arg Ser
1               5

(2) INFORMATION FOR SEQ ID NO: 56:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 56:

Arg Thr Thr Ser Arg Gly
1               5

(2) INFORMATION FOR SEQ ID NO: 57:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 57:

Arg Glu Lys Lys Phe Phe
1               5

(2) INFORMATION FOR SEQ ID NO: 58:

(i) SEQUENCE CHARACTERISTICS:
            (A) LENGTH: 6 amino acids
            (B) TYPE: amino acid
            (C) STRANDEDNESS: single (D) TOPOLOGY: linear (ii) MOLECULE TYPE: peptide (xi) SEQUENCE DESCRIPTION: SEQ ID NO: 58:

Lys Glu Leu Lys Gly Gly
1               5

(2) INFORMATION FOR SEQ ID NO: 59:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 59:

Asp Lys Lys Ser Lys Thr
1               5

(2) INFORMATION FOR SEQ ID NO: 60:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 60:

Gly Pro Ala Ser Lys Ser
1               5

(2) INFORMATION FOR SEQ ID NO: 61:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa =
                N(a)-9-fluorenyl-methyloxycarbonylglycine"

(xi) SEQUENCE DESCRIPTION: SEQ ID NO: 61:

Xaa Asn Trp His Gly Thr Ala Pro
1               5

(2) INFORMATION FOR SEQ ID NO: 62:

(i) SEQUENCE CHARACTERISTICS:
            (A) LENGTH: 10 amino acids
            (B) TYPE: amino acid
            (C) STRANDEDNESS: single
            (D) TOPOLOGY: /note= "Xaa = tryptophan benzyl
                ester"

(ii) MOLECULE TYPE: peptide (ix) FEATURE:
            (A) NAME/KEY: Modified-site
            (B) LOCATION: 10

(xi) SEQUENCE DESCRIPTION: SEQ ID NO: 62:

Gly Asn Trp His Gly Thr Ala Pro Asp Xaa
1               5                   10

(2) INFORMATION FOR SEQ ID NO: 63:

(i) SEQUENCE CHARACTERISTICS:
        (A) LENGTH: 10 amino acids
        (B) TYPE: amino acid
        (C) STRANDEDNESS: single
        (D) TOPOLOGY: /note= "Xaa = tryptophan benzyl
            ester"

(ii) MOLECULE TYPE: peptide (ix) FEATURE:
        (A) NAME/KEY: Modified-site
        (B) LOCATION: 1
        (D) OTHER INFORMATION: /note=
            "N(a)-9-fluorenyl-methyloxycarbonylglycine"

(ix) FEATURE:
        (A) NAME/KEY: Modified-site
        (B) LOCATION: 9
        (D) OTHER INFORMATION: /note= "(B)-t-butyl aspartate"

(ix) FEATURE:
        (A) NAME/KEY: Modified-site
        (B) LOCATION: 10

(xi) SEQUENCE DESCRIPTION: SEQ ID NO: 63:

Xaa Asn Trp His Gly Thr Ala Pro Xaa Xaa
1               5                   10

(2) INFORMATION FOR SEQ ID NO: 64:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

Val Thr Gly Arg Gly Asp Ser Pro Ala
1               5

(2) INFORMATION FOR SEQ ID NO: 65:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "Xaa=alaninamide"

(xi) SEQUENCE DESCRIPTION: SEQ ID NO: 65:

Val Tyr Ala Val Thr Gly Arg Gly Asp Ser Pro Xaa
1               5                   10

(2) INFORMATION FOR SEQ ID NO: 66:

(i) SEQUENCE CHARACTERISTICS:
        (A) LENGTH: 9 amino acids

```
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

Ser Met Gly Leu Pro Cys Val Val Met
1               5

(2) INFORMATION FOR SEQ ID NO: 67:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

Ser Ser Gly Cys Val Leu Ser
1               5

(2) INFORMATION FOR SEQ ID NO: 68:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

Ser Met Gly Leu Pro Cys Ile Phe Met
1               5

(2) INFORMATION FOR SEQ ID NO: 69:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 8
        (D) OTHER INFORMATION: /note= "isoleucinamide"

(xi) SEQUENCE DESCRIPTION: SEQ ID NO: 69:

Phe Gly Gly Arg Ile Asp Arg Xaa
1               5

(2) INFORMATION FOR SEQ ID NO: 70:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 12
        (D) OTHER INFORMATION: /note= "alaninamide"
```

(xi) SEQUENCE DESCRIPTION: SEQ ID NO: 70:

Ala Phe Gly Gly Arg Ile Asp Arg Ile Gly Ala Xaa
1               5                   10

(2) INFORMATION FOR SEQ ID NO: 71:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /note= "N-methyl-L-isoleucine"

(ix) FEATURE:
        (A) NAME/KEY: Modified-site
        (B) LOCATION: 8
        (D) OTHER INFORMATION: /note= "isoleucinamide"

(xi) SEQUENCE DESCRIPTION: SEQ ID NO: 71:

Phe Gly Gly Arg Xaa Asp Arg Xaa
1               5

(2) INFORMATION FOR SEQ ID NO: 72:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "D-Arg"

(ix) FEATURE:
        (A) NAME/KEY: Modified-site
        (B) LOCATION: 4
        (D) OTHER INFORMATION: /note= "Hyp"

(ix) FEATURE:
        (A) NAME/KEY: Modified-site
        (B) LOCATION: 8
        (D) OTHER INFORMATION: /note= "D-Phe"

(xi) SEQUENCE DESCRIPTION: SEQ ID NO: 72:

Xaa Arg Pro Xaa Gly Phe Cys Xaa Leu Arg
1               5                   10